United States Patent [19]
Sasaki

[11] Patent Number: 5,882,331
[45] Date of Patent: Mar. 16, 1999

[54] METHODS FOR PUNCTURING AN ORGAN WITHIN A BODY CAVITY

[76] Inventor: Hiroshi Sasaki, 14-9, Nishitaka 2-chome, Bunkyo-ku, Tokyo 113, Japan

[21] Appl. No.: 882,897

[22] Filed: Jun. 26, 1997

Related U.S. Application Data

[62] Division of Ser. No. 574,379, Dec. 18, 1995.

[30] Foreign Application Priority Data

May 26, 1995 [JP] Japan ................................. 7-128439

[51] Int. Cl.⁶ .................................................. A61M 31/00
[52] U.S. Cl. .......................... 604/51; 604/264; 604/164; 604/167; 604/180; 604/200; 128/898; 600/577; 600/109; 606/108
[58] Field of Search .................................. 604/27–29, 30, 604/35, 41, 46–49, 51, 122, 268, 272, 264, 265, 280, 256, 104–106, 164, 167, 169, 170, 174, 175, 176, 180, 181, 187, 200, 201, 204, 205, 244, 245; 128/DIG. 26, 898, 897, 899; 606/167, 184, 185, 108; 600/573–583, 184, 101, 104, 109, 114

[56] References Cited

U.S. PATENT DOCUMENTS

| | | |
|---|---|---|
| 1,934,046 | 11/1933 | Demarchi . |
| 3,253,594 | 5/1966 | Matthews et al. . |
| 3,540,431 | 11/1970 | Mobin-Uddin . |
| 3,605,747 | 9/1971 | Pashkow . |
| 4,692,139 | 9/1987 | Stiles . |
| 5,002,557 | 3/1991 | Hasson . |
| 5,011,488 | 4/1991 | Ginsburg . |
| 5,073,166 | 12/1991 | Parks et al. . |
| 5,137,520 | 8/1992 | Maxson et al. . |
| 5,176,648 | 1/1993 | Holmes et al. ........................ 604/180 |
| 5,176,662 | 1/1993 | Bartholomew et al. . |
| 5,257,973 | 11/1993 | Villasuso . |
| 5,267,960 | 12/1993 | Hayman et al. . |
| 5,282,788 | 2/1994 | Wilk et al. . |
| 5,312,351 | 5/1994 | Gerrone . |
| 5,352,210 | 10/1994 | Marrucchi ............................. 604/180 |
| 5,352,211 | 10/1994 | Merskelly . |
| 5,366,446 | 11/1994 | Tal et al. ................................ 604/180 |
| 5,370,625 | 12/1994 | Schichman . |
| 5,375,588 | 12/1994 | Yoon ..................................... 604/180 |
| 5,409,466 | 4/1995 | Watson et al. . |
| 5,549,626 | 8/1996 | Miller et al. . |
| 5,575,794 | 11/1996 | Walus et al. . |

*Primary Examiner*—Ronald Stright
*Attorney, Agent, or Firm*—Morgan & Finnegan, L.L.P.

[57] ABSTRACT

The present invention relates to a puncture method and a puncture system. More specifically, the objective of the present invention is to carry out the aspiration of a sample from a human organ or an animal organ and the inner examination thereof, without the outward leak of the fluid and the like in the organ.

The puncture method and puncture system of the present invention is in the following structure; making a parasol part arranged on a reservoir adhere through an adhesive to the site to be punctured, inserting a needle body through a sealing part of the reservoir into the site to be punctured to draw out the inner fluid, the leak of the fluid can be prevented by the reverse operation of the sealing part.

29 Claims, 35 Drawing Sheets

METHODS FOR PUNCTURING AN ORGAN WITHIN A BODY CAVITY

This application is a continuation, of application Ser. No. 08/574,379, filed Dec. 18, 1995, now allowed.

BACKGROUND OF THE INVENTION

1. Field of the Invention

The present invention relates to a puncture method and a puncture system. More specifically, the present invention relates to a novel modification thereof to carry out the aspiration of a sample from an organ and the examination of the inner conditions of the organ without the outward leak of the fluid and the like in the organ of human bodies and animals.

2. Description of the Prior Art

A puncture method generally comprising puncturing a site to be punctured in an organ with an injection needle and aspirating the inner fluid and the like for pathological examination of the fluid and the like, has been employed conventionally.

Because the conventional puncture method has been conducted as described above, the following problems have been remarked.

When an injection needle is inserted into a site to be punctured to aspirate and then withdraw the fluid and the like, an opening remains at the site punctured so that the fluid and the like may leak into bodies, eventually causing the metastasis of the fluid into other organs if the fluid is malignant.

SUMMARY OF THE INVENTION

The object of the present invention is to provide a puncture method and a puncture system for aspirating a sample from an organ and examining the inner conditions of the organ without leaking fluid and the like from the organ of human bodies and animals.

By the puncture method and the puncture system in accordance with the present invention, the puncture system is inserted through an opening formed on the wall body of a human body or an animal body to push in only a first tubular body. A parasol part and a reservoir are then sprung out from a second tubular body, whereby the parasol part is opened from a compact, flooded shape into an original parasol shape. The surface of a site to be punctured is dried by means of a drying means inserted from another direction and thereafter adhesive is fed by scission of a bag part, removal of a plug or other adhesive feeding jigs onto the site to be punctured or the parasol part to obtain a final film thickness of about 0.1 to 0.2 mm.

At the state described above, pushing inwardly the whole system, the parasol part gets in close contact with the site to be punctured, so that the two are integrated by means of the action of the adhesive.

Inserting a needle body into the first tubular body punctures a sealing part to then pass through the site to be punctured. Drawing out only a bar-like needle part from the tubular needle part and inserting an aspirator into the head of the tubular needle part for aspiration, the fluid and the like in the site to be punctured can be aspirated and drawn out. Cutting the tubular body immediately after completion of such aspiration, the parasol part and a part of the tubular body remain on the site to be punctured, along with the compaction of the sealing part to recover the original shape, so that the opening made during puncturing with the needle body disappears and the opening formed on the site to be punctured is completely occluded with the sealing part, whereby the outward leak of inner fluid can be prevented. Thus, the metastasis of a malignant cancer via such leak to other organs can be prevented.

By inserting a camera or a sample collector instead of the aspirator described above, the inside of the site to be punctured can be observed or a biological sample can be collected.

DESCRIPTION OF THE PREFERRED EMBODIMENTS

The puncture method and puncture system of the present invention will now be explained in detail below with reference to the drawings.

Figure 1:
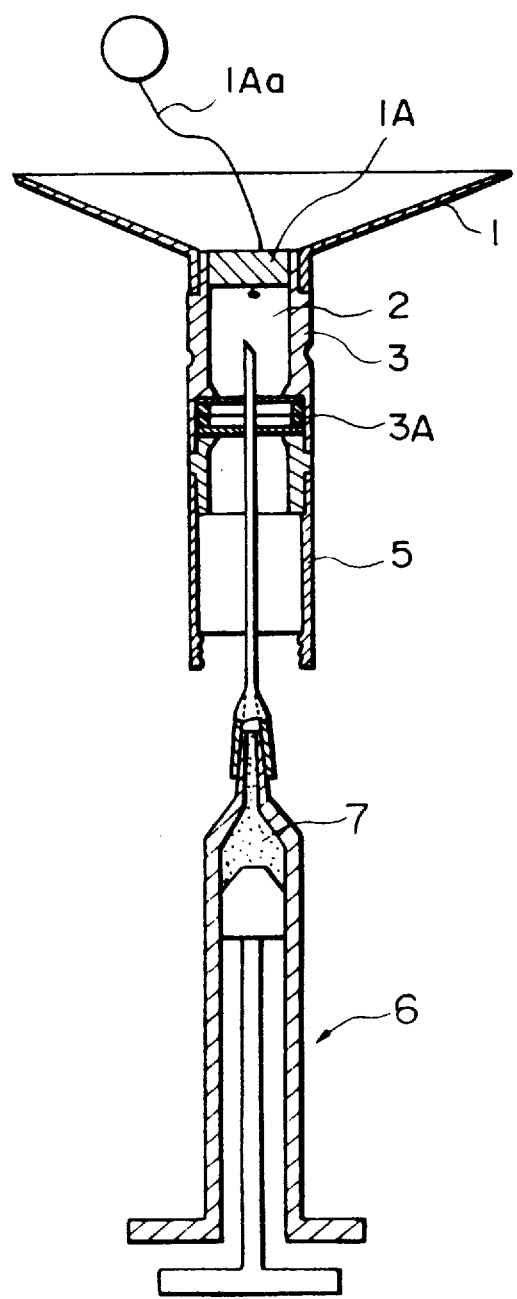
FIG. 1 depicts the sectional view of the principal part of the puncture system in accordance with the present invention.
Figure 2:
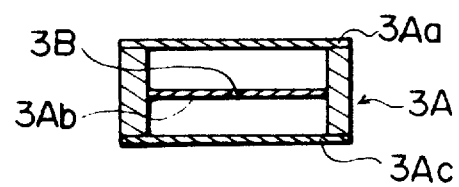
FIG. 2 depicts the enlarged sectional view of the sealing part of FIG. 1.
Figure 3:
FIG. 3 depicts the sectional view showing another example of FIG. 2.
Figure 4:
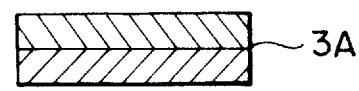
FIG. 4 depicts the sectional view showing still another example of FIG. 2.

FIG. 1 shows the principal part of the puncture system; of the first embodiment "1" represents a parasol part in a parasol shape composed of urethane rubber; a tubular body 3 containing a adhesive reservoir 2 is integrally formed (may be also formed separately) at the position of the axial center of the the parasol part 1; and the reservoir 2 is composed of stopper 1A and sealing part 3A, arranged in a sealing fashion on the tubular body 3. Herein, the tubular body 3, the parasol part 1 and the sealing part 3A may be integrally molded, or they may be composed of separate parts and then integrally connected together. The stopper 1A is composed of rubber and the like, arranged in a removable manner on the tubular body 3. By pulling wire 1Aa connected with the stopper 1A, the stopper 1A can be removed from the tubular body 3. As shown in FIG. 2, the sealing part 3A is composed of first and third films 3Aa and 3Ac arranged at the both ends in the axial direction and second film 3Ab positioned intermediately between them, and a cross-cut 3B is formed on the second film 3Ab so that the needle and the like described below might readily pass through the sealing part 3A. Furthermore, the structure of the sealing part 3A comprises not only such three layers but also a single layer or two layers. Further, there may be provided the sealing part 3A as shown in FIGS. 3 and 4.

On the tubular body 3, there is arranged screw body 5 of a tubular form comprising corrosion-resistant aluminium and the like. Adhesive 7 such as surgical Allon-alfa and the like (other adhesives may be used as well) is injected into the reservoir 2 by means of injector 6, immediately prior to use. Without using the injector 6, adhesive 7 may be fed into the reservoir 2 after removing the stopper 1A. Incidentally, it is preferable to set an amount of this adhesive to 0.1cc through 2.0cc.

A tubular body 9 of nearly the same outer diameter as that of the screw body 5, comprising corrosion-resistant aluminium and the like and having also first holder 8, is helically connected in series connection with the screw body 5. Furthermore, the tubular body 9 may be directly or indirectly connected with the tubular body 3, integrally or in a separate fashion.

Figure 6:
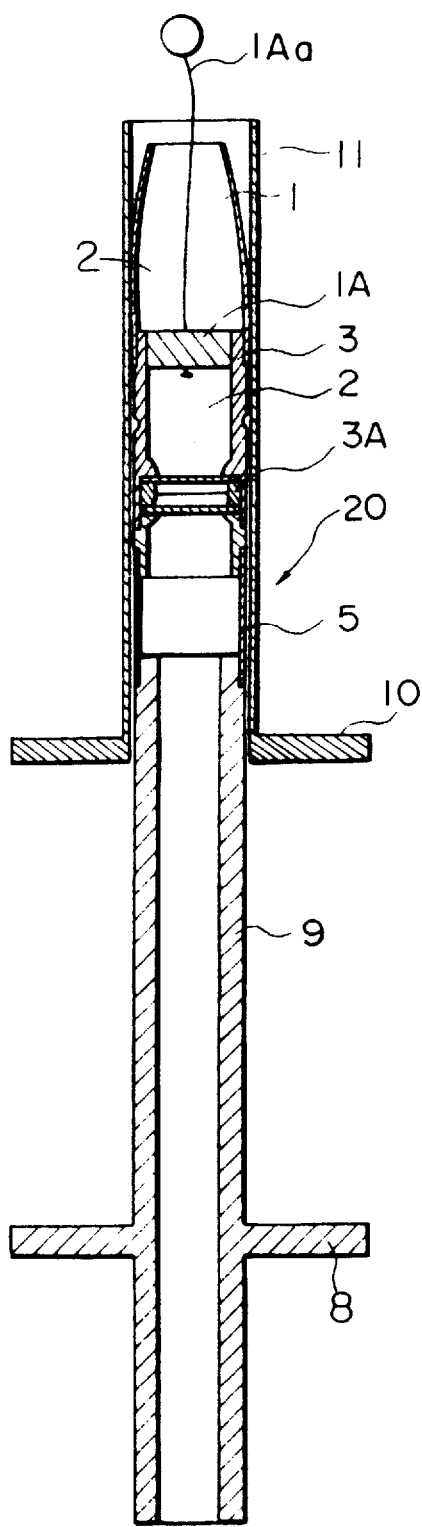
FIG. 6 depicts the structural view showing a second tubular body.

As shown in FIG. 6, the tubular body 9 connected with the screw body 5 has a second holder 10, and is inserted along the coaxial direction into a second tubular body 11 comprising corrosion-resistant aluminium and the like. Thus, the puncture system 20 in accordance with the present invention is depicted in the state of completion in FIG. 6. At the state, this parasol part 1 is compressed into a more compact shape and is contained in the second tubular body 11. As shown in FIG. 1, the parasol body 1 is composed of urethane rubber and the like; and the tubular body 3 is composed of silicone rubber, a resin and the like.

Figure 7:
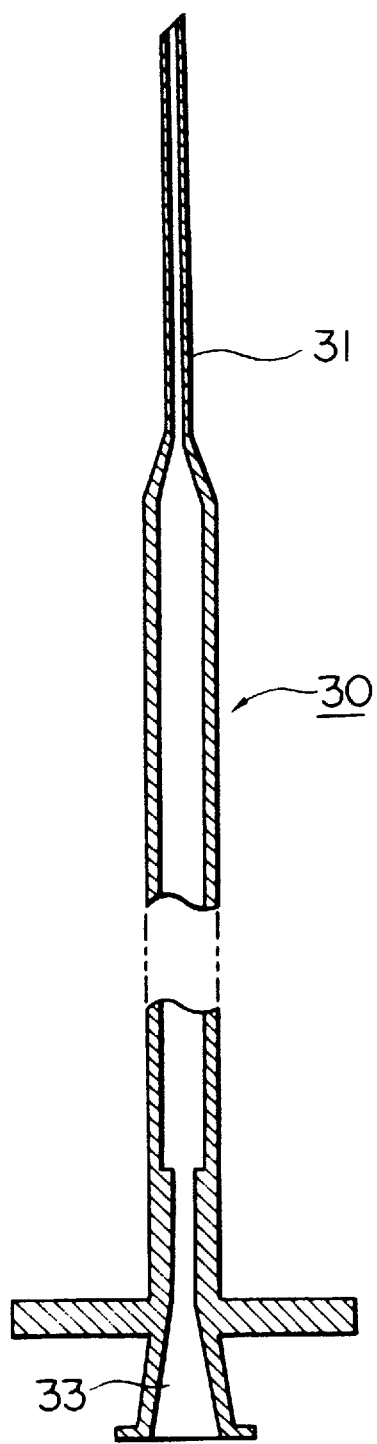
FIG. 7 depicts the sectional view showing the tubular needle part of the needle body.
Figure 8:
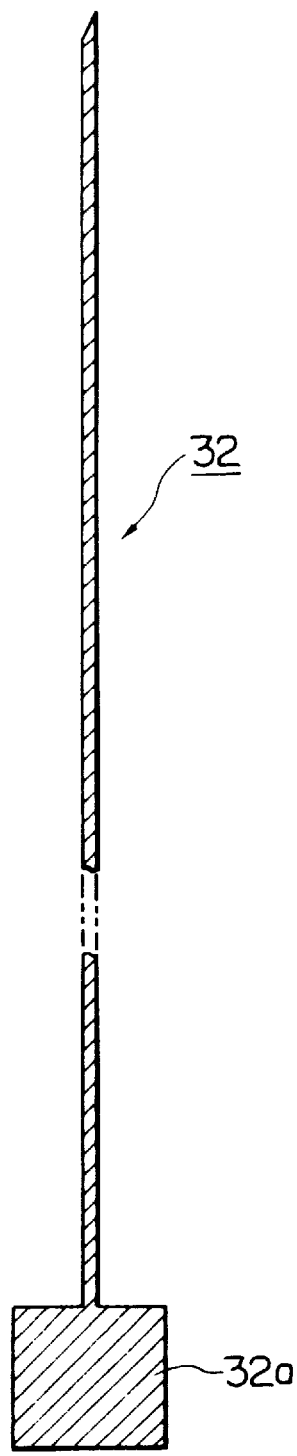
FIG. 8 depicts the sectional view showing the bar-like needle part.
Figure 9:
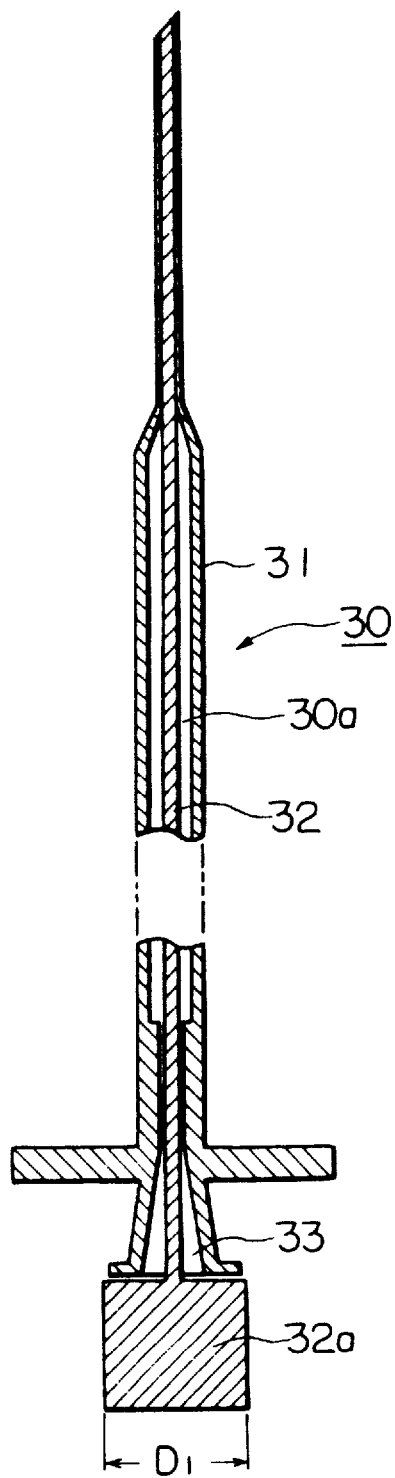
FIG. 9 depicts the sectional view of the needle body.
Figure 10:
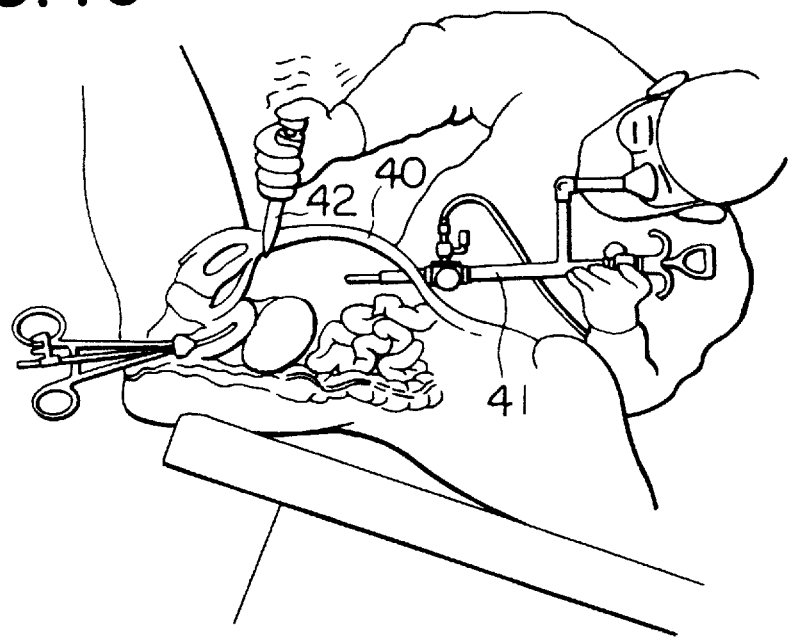
FIG. 10 depicts the compositional view of a woman's abdomen showing a step in a puncture method for use in the treatment of ovarian cancer, wherein a trocar is being inserted into the abdomen.
Figure 11:
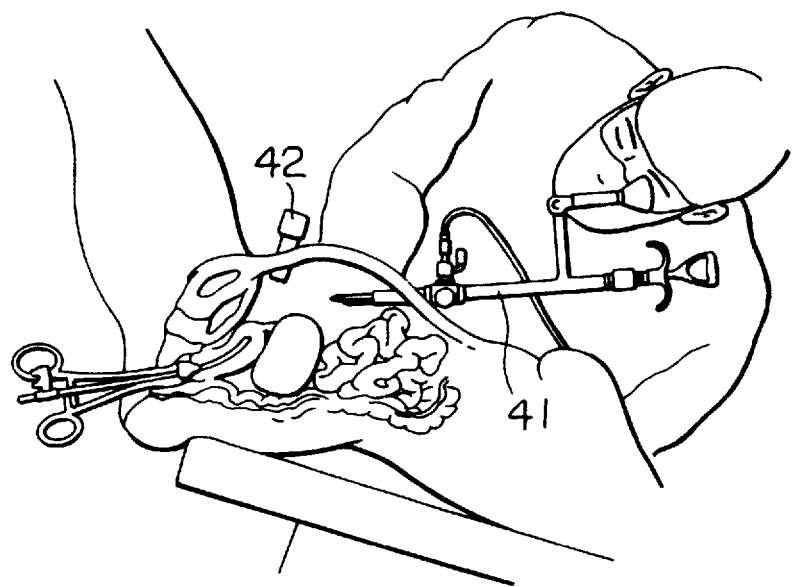
FIG. 11 depicts the compositional view of the woman's abdomen after insertion of the trocar.
Figure 12:
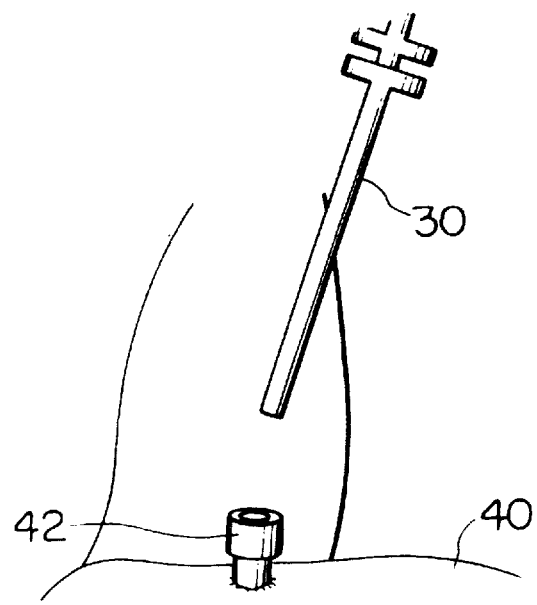
FIG. 12 depicts a next step in the puncture method wherein the puncture system is inserted into the trocar.

FIGS. 7 to 9 depict the structure of a needle body 30 to be used in the puncture system 20 shown in FIG. 6 described above; FIG. 7 depicts a tubular needle part 31; and FIG. 8 depicts a bar-like needle part 32 to be inserted into the tubular needle part 31. Taper-like insertion part 33 is formed on the rear end of the tubular needle part 31, and by inserting the bar-like needle part 32 through the insertion part 33 into the tubular needle part 31, a guide hole 30a inside the tubular needle part 31 is occluded. By forming a diameter D1 of an expanded part 32a formed on the rear part of the bar-like needle part 32 far larger than the bore diameter of the insertion part 33, the insertion part 33 can be occluded structurally by means of the expanded part 32a. Furthermore, the needle body 30 is entirely coated with silicone coating.

Description of puncturing a human organ or an animal organ by means of the structure described above, follows. The area to be punctured is the site of human ovarian cancer.

Figure 13:
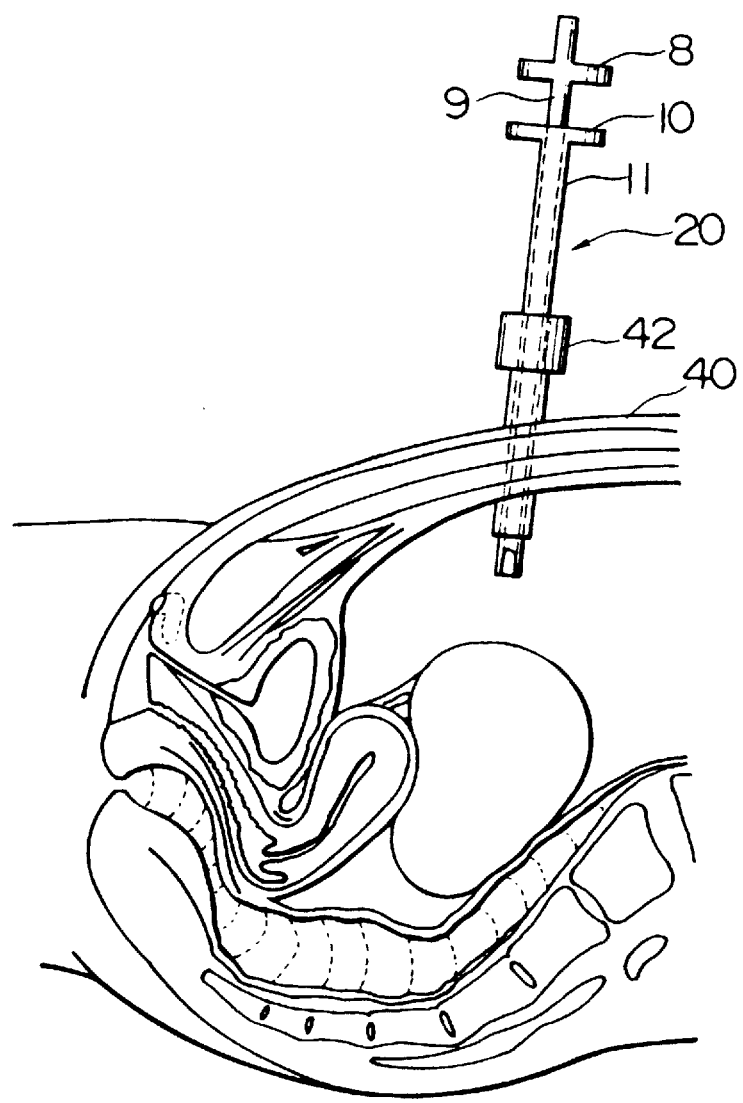
FIG. 13 depicts the longitudinal sectional view in the abdomen after insertion of the puncture system.
Figure 14:
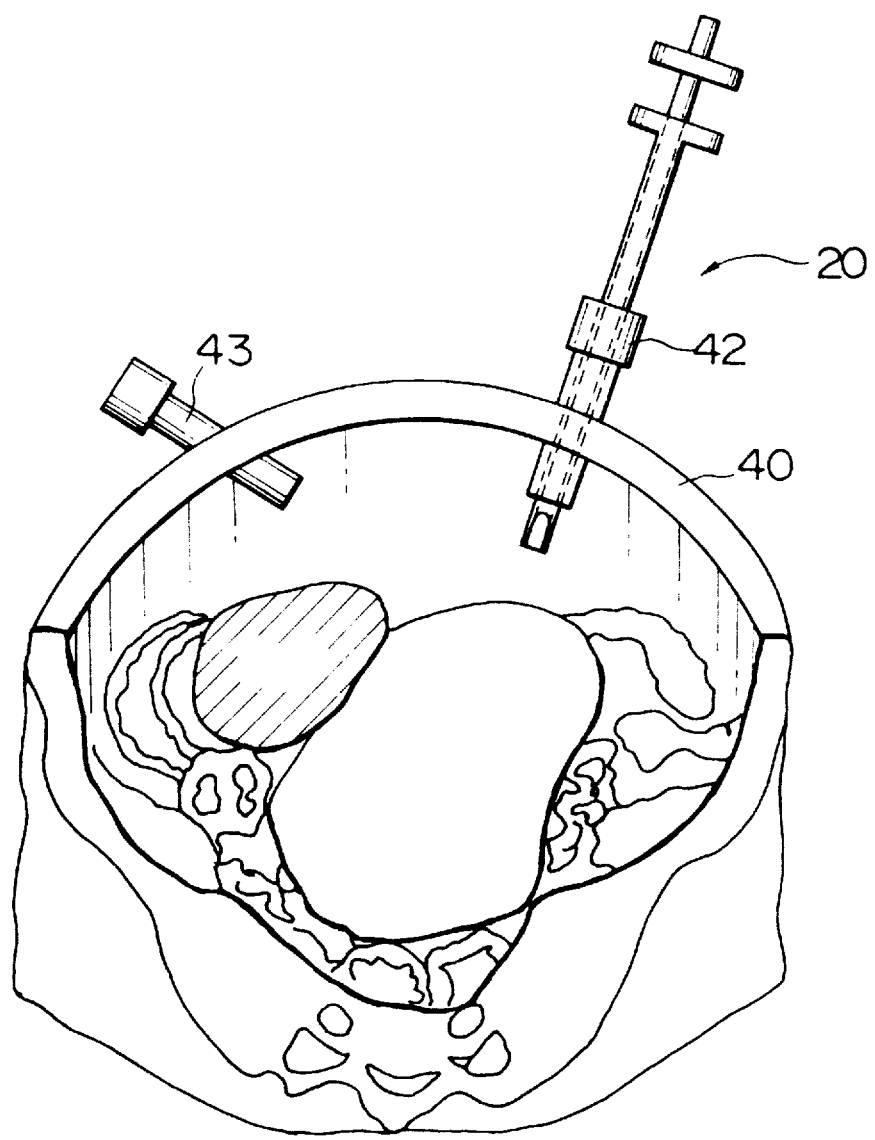
FIG. 14 depicts the transverse sectional view of the abdomen after insertion of the puncture system through the trocar.
Figure 15:
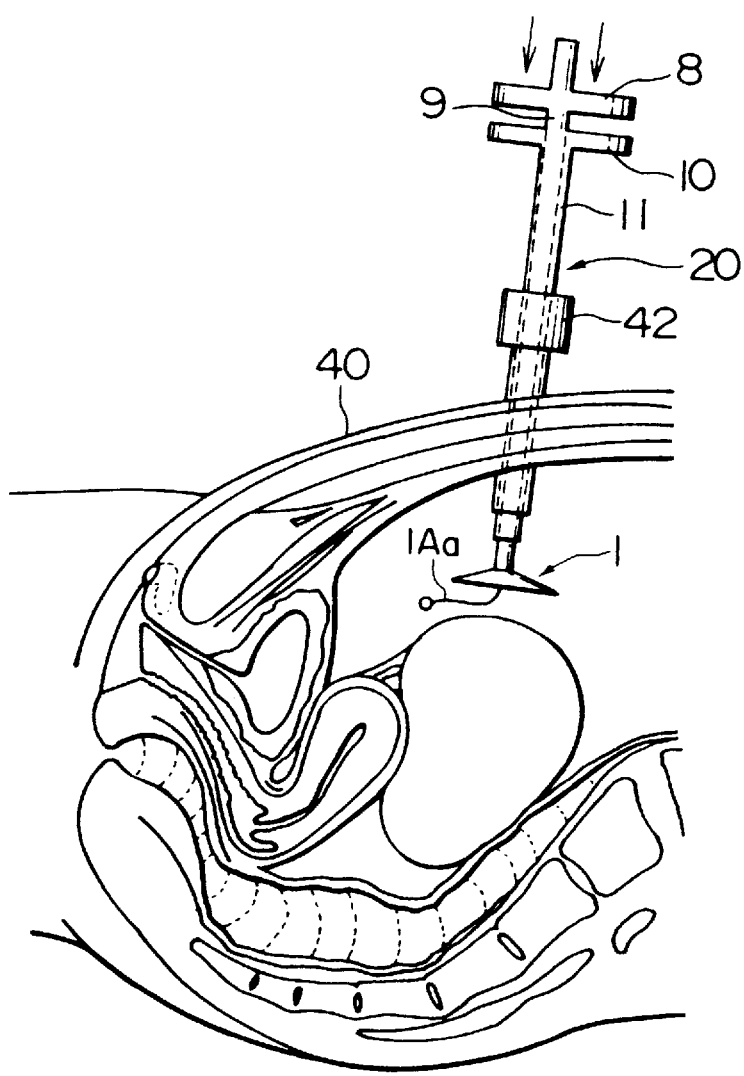
FIG. 15 depicts the longitudinal sectional view in abdomen after deployment of the parasol.

As shown in FIGS. 10 to 14, a laparascope 41 is inserted into the wall body 40 for expansion under gas supply, to stand up tubular first trocar 42. As shown in FIGS. 13 and 14, inserting the puncture system 20 of the present invention through the first trocar 42 into the wall of the body 40 to push in only the tubular body 9 as shown in FIG. 15, parasol part 1 is pushed outside from the inside of the second tubular body 11. Then, the parasol part 1 is opened from the compact shape into the original parasol shape.

Figure 16:
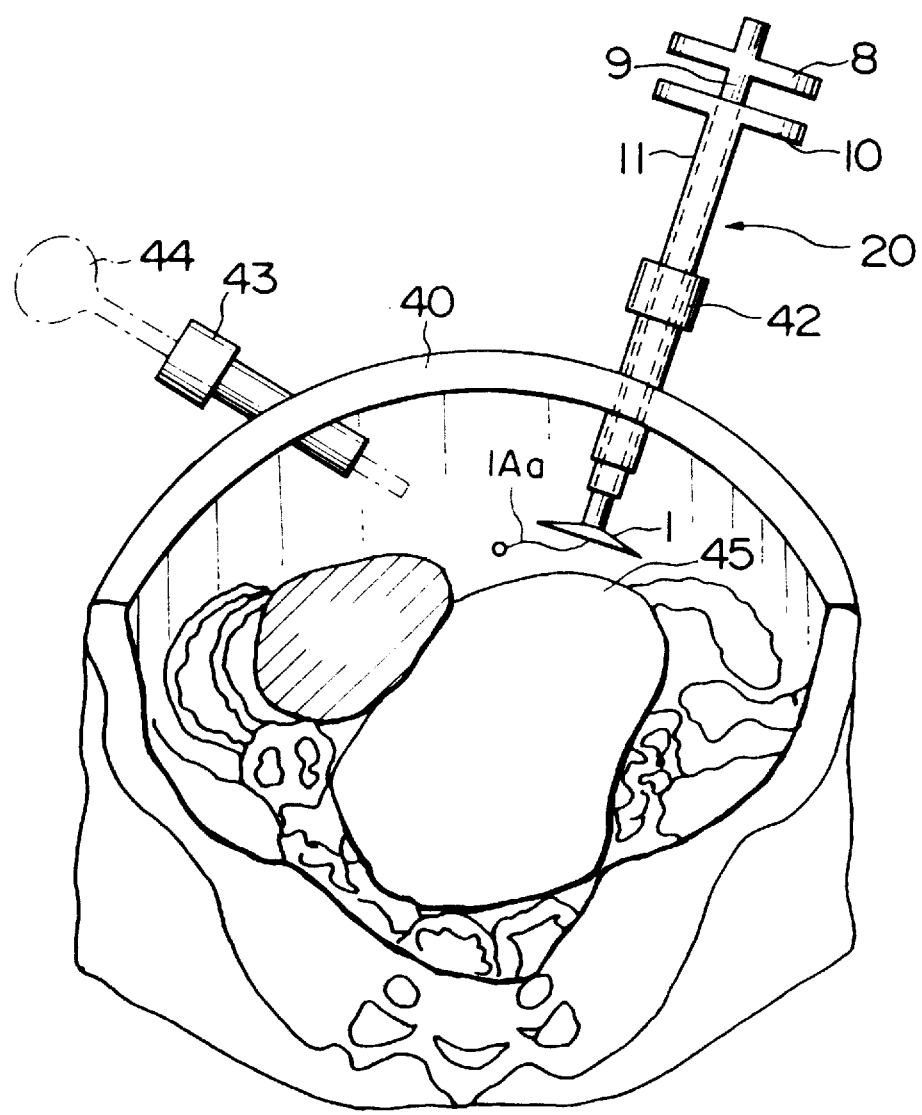
FIG. 16 depicts the transverse sectional view of FIG. 15, showing the drying means in phantom.
Figure 17:
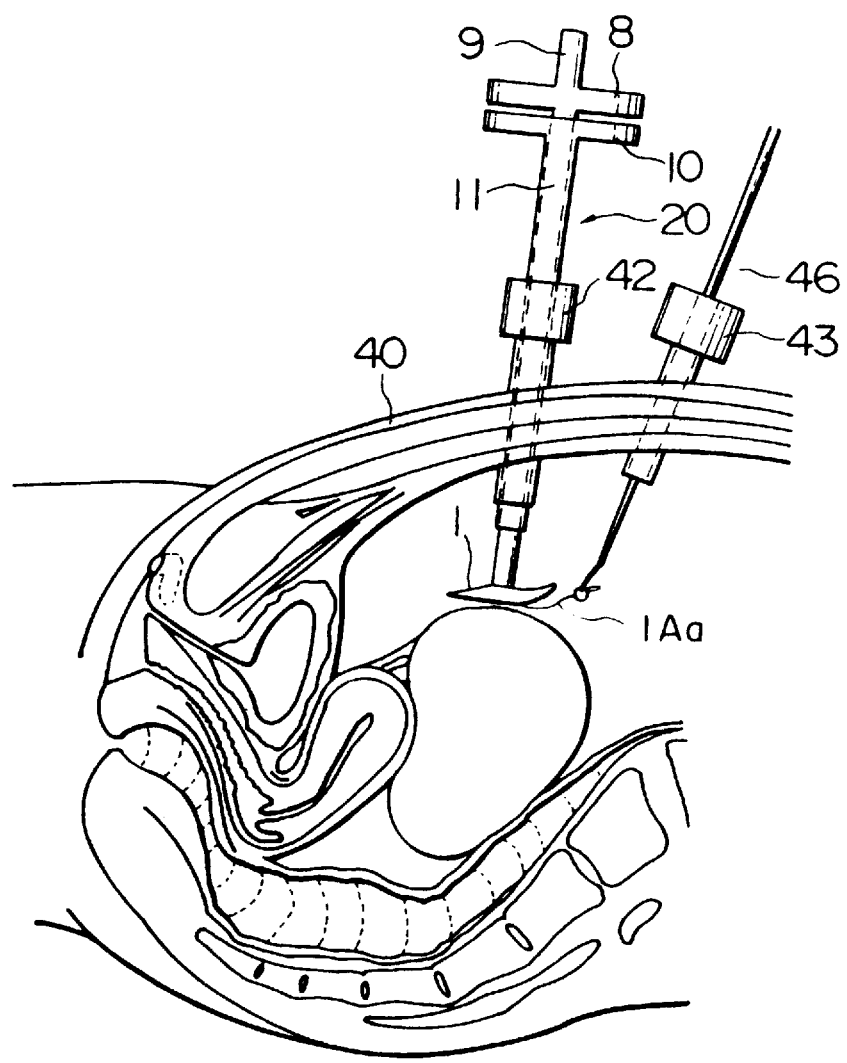
FIG. 17 depicts the longitudinal sectional view of the abdomen during cutting of the bag part.
Figure 18:
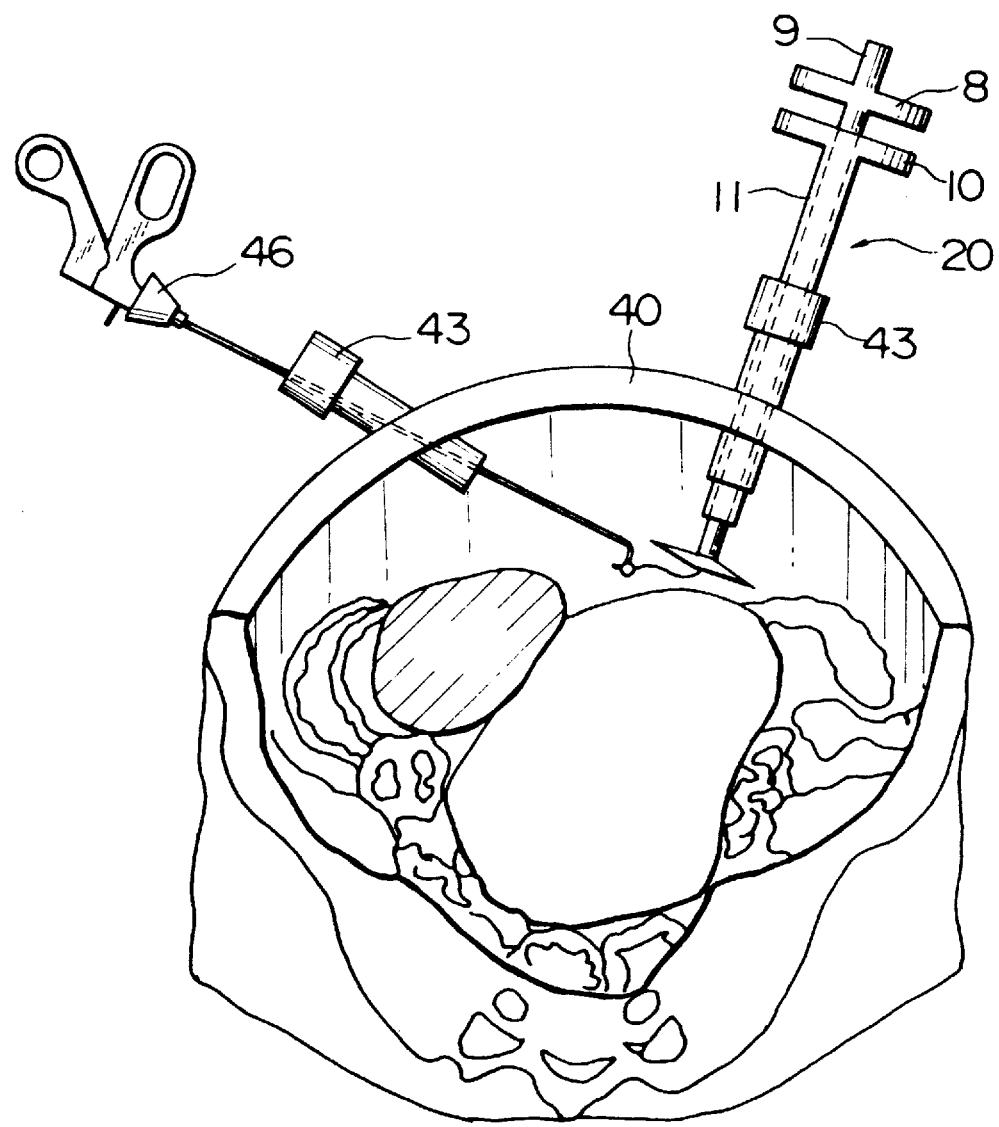
FIG. 18 depicts the transverse sectional view of FIG. 17, further illustrating the cutting means.

As shown in FIG. 16, using drying means 44 for supplying dry air or gas through second trocar 43 inserted into the wall body 40 from the other direction, the surface of an ovarian cancer site to be punctured 45, for example, is dried. Subsequently, the drying means 44 is withdrawn from the second trocar to, inserting hooking means 46 s inserted through the second trocar 43 instead and the wall body 40, for pulling wire 1Aa as shown in FIGS. 17 and 18. Stopper 1A is removed by the hooking means to supply adhesive 7 onto the site to be punctured 45. Additionally, the adhesive 7 should be injected primarily into the reservoir 2, immediately prior to surgery.

Figure 19:
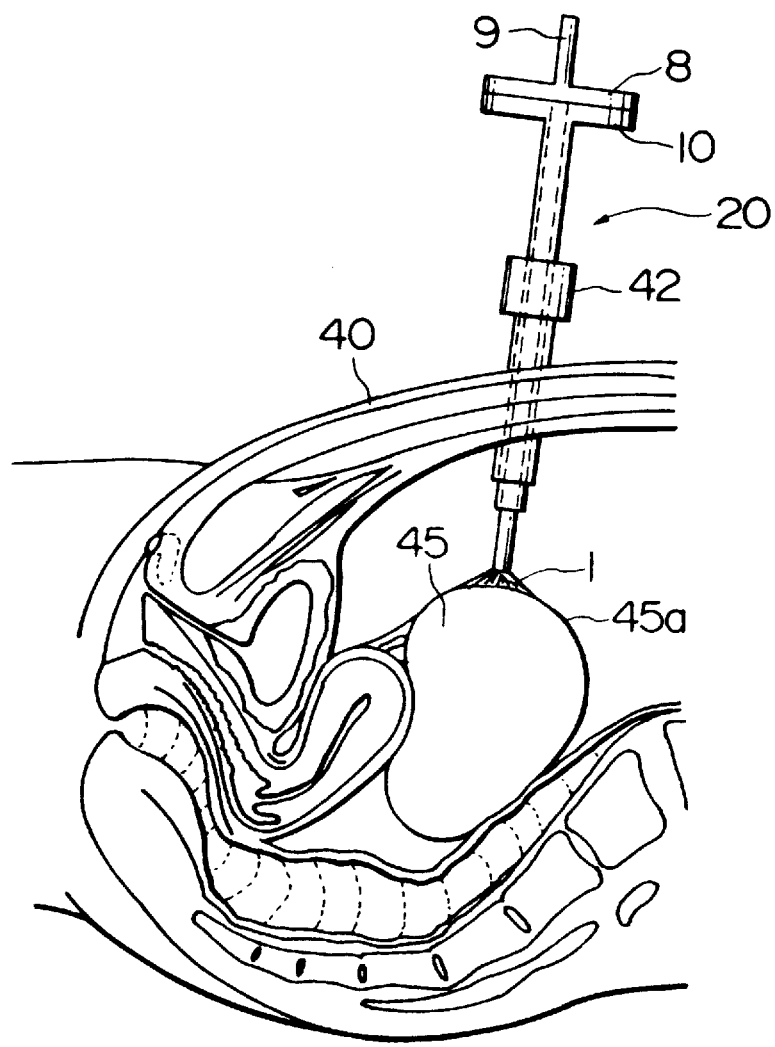
FIG. 19 depicts the longitudinal sectional view of the abdomen showing the parasol part in adhesion to the site to be punctured.
Figure 20:
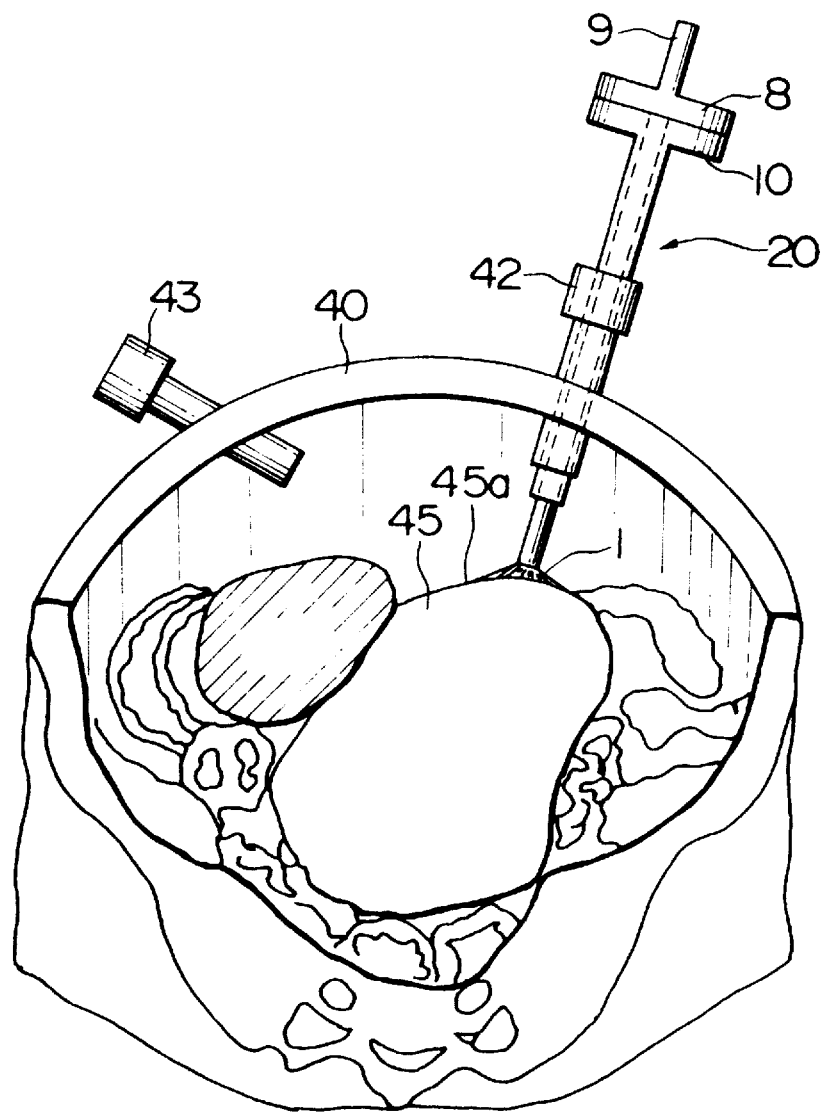
FIG. 20 depicts the transverse sectional view of FIG. 19.
Figure 21:
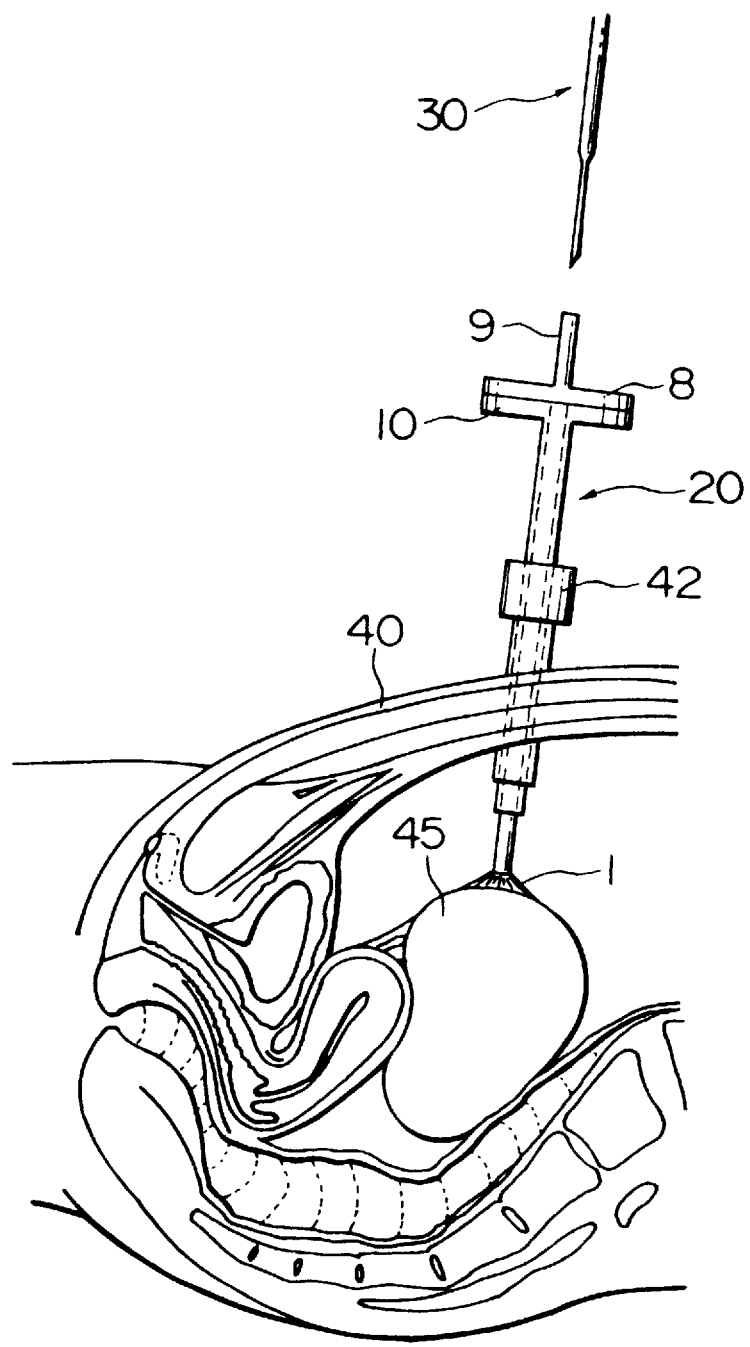
FIG. 21 depicts the longitudinal sectional view of the abdomen immediately prior to puncturing.
Figure 22:
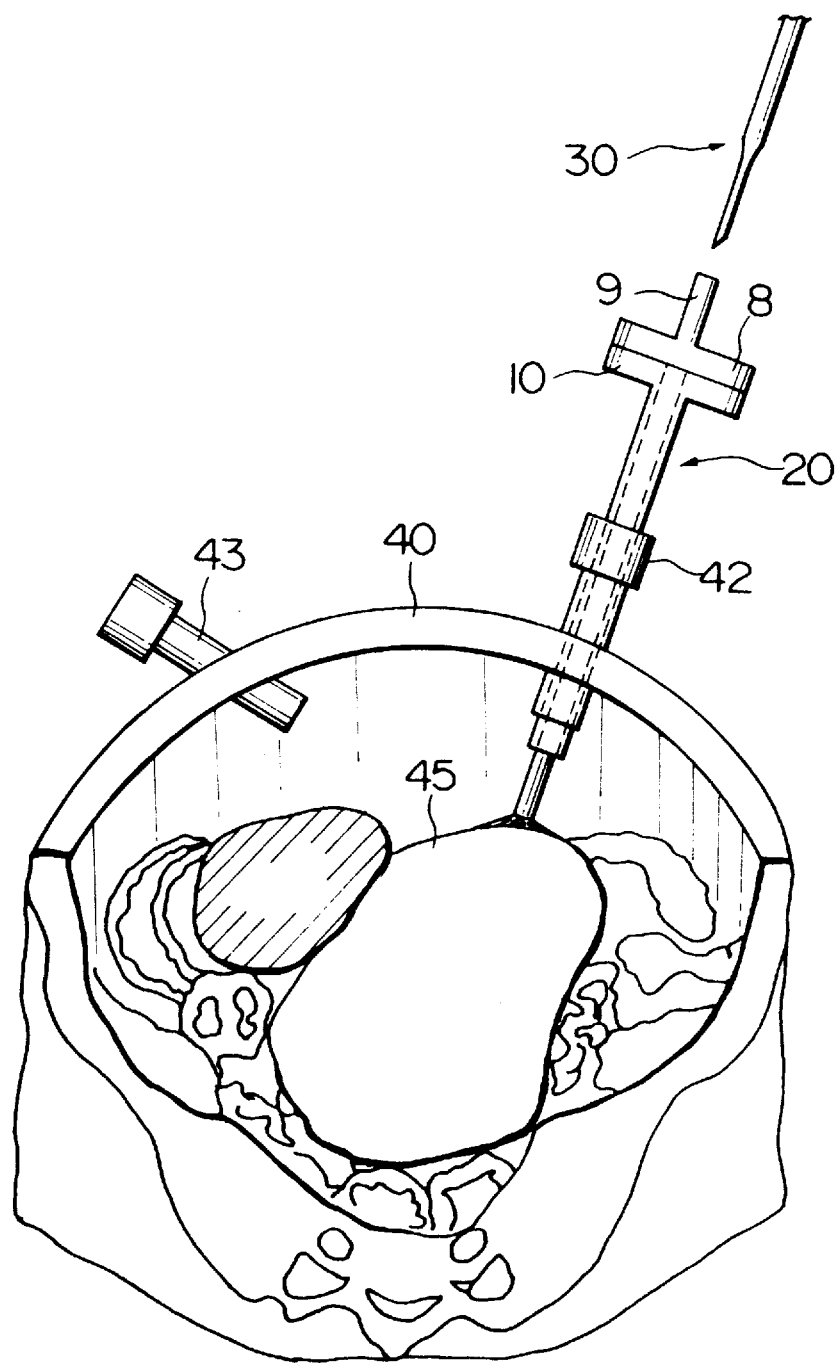
FIG. 22 depicts the transverse sectional view of FIG. 21.
Figure 23:
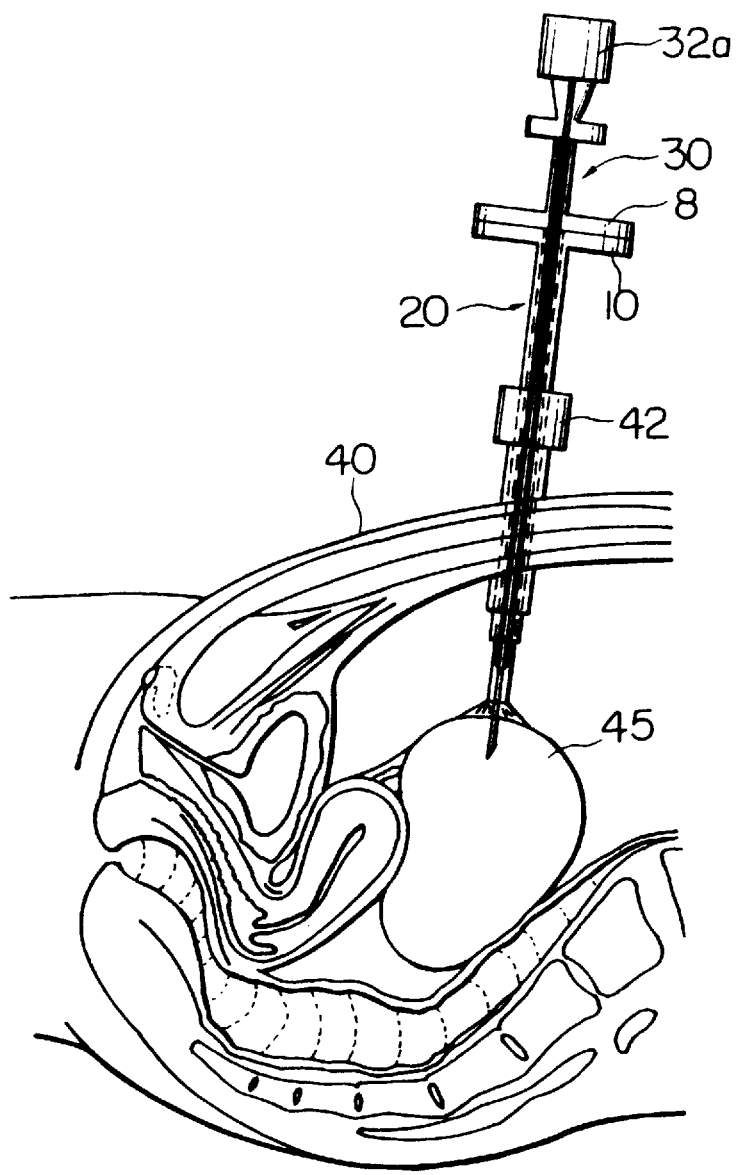
FIG. 23 depicts the longitudinal sectional view of the puncturing state abdomen, wherein the site of the cancer is punctured.
Figure 24:
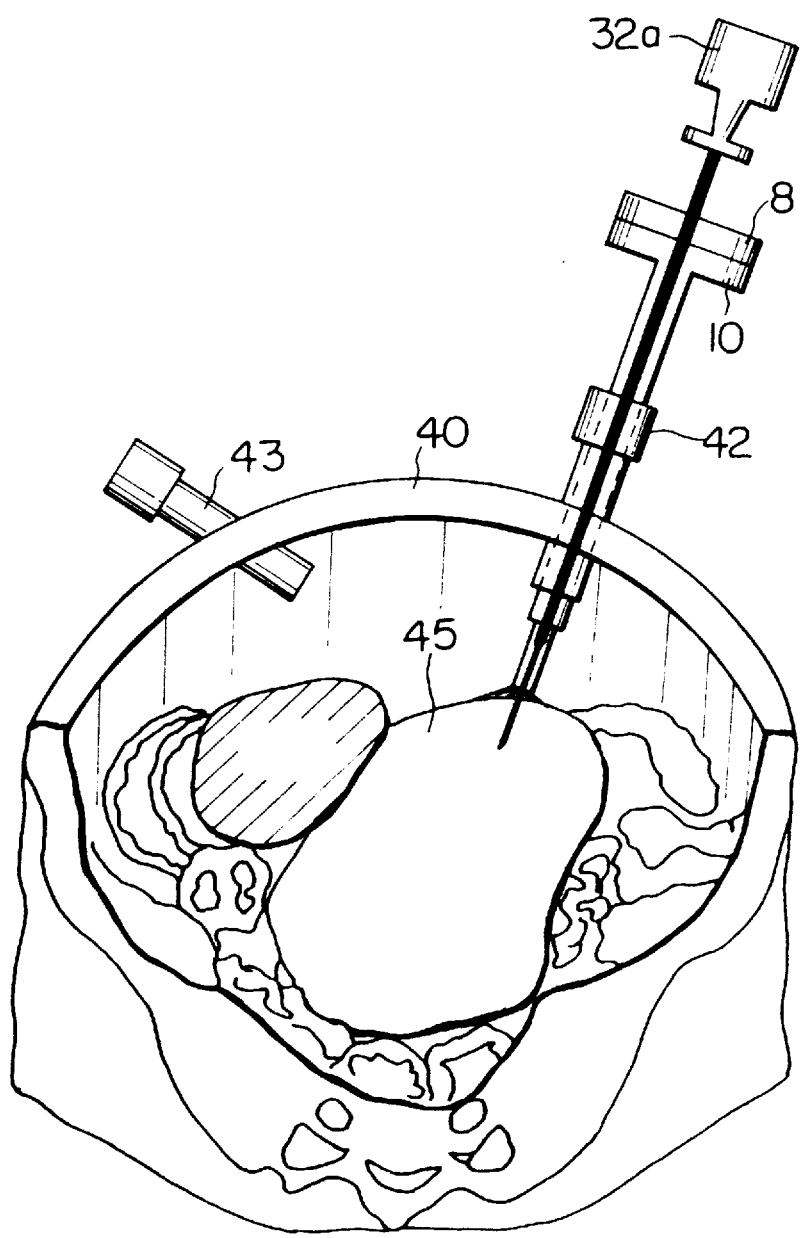
FIG. 24 depicts the transverse sectional view of FIG. 23.

As shown in FIGS. 19 and 20, pushing the puncture system 20 through the wall body 40, the parasol part 1 is fixed through the adhesive 7 onto the surface 45a of the site to be punctured 45. As shown in FIGS. 21 and 22, needle body 30 is inserted into the puncture system 20 while the parasol part 1 is in that state. As shown in FIGS. 23 and 24, then, the needle body 30 is passed through sealing part 3A, so that the tip of the needle body 30 can be inserted into the site to be punctured 45.

Figure 25:
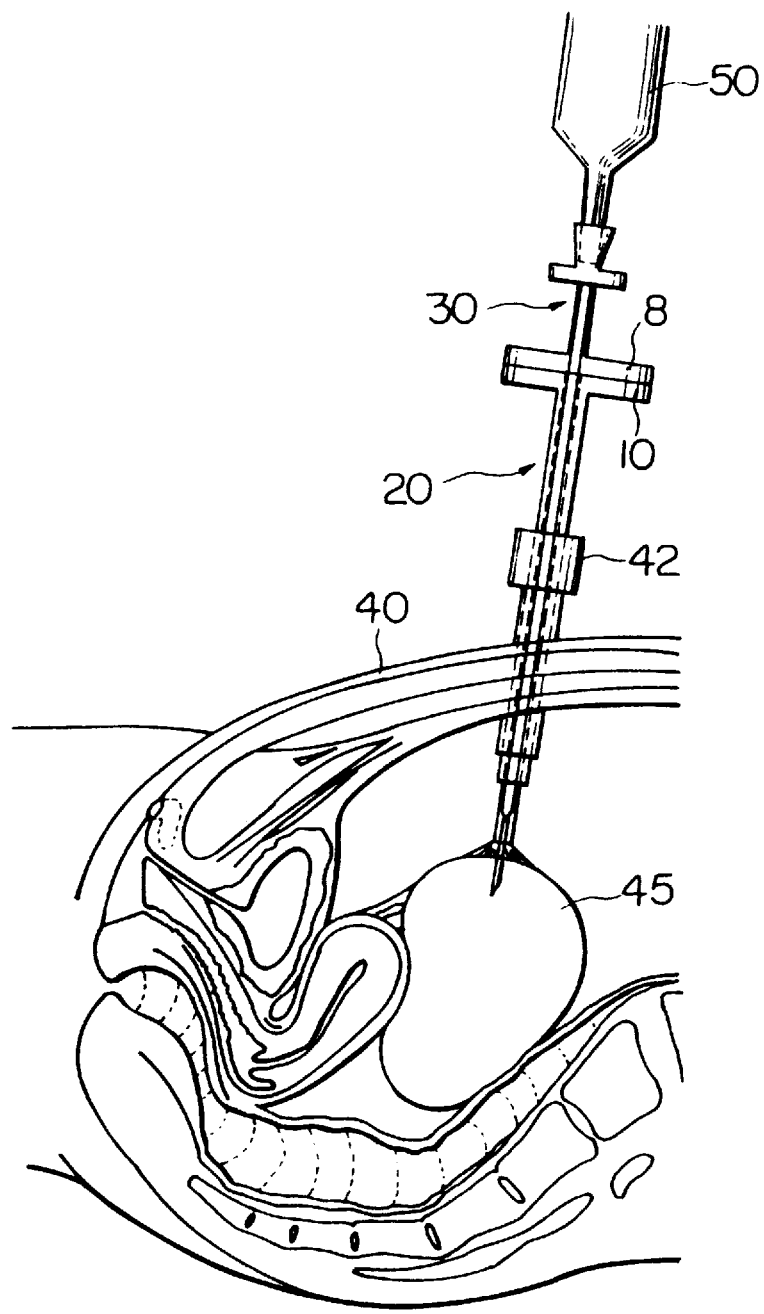
FIG. 25 depicts the longitudinal sectional view of the abdomen during aspiration.
Figure 26:
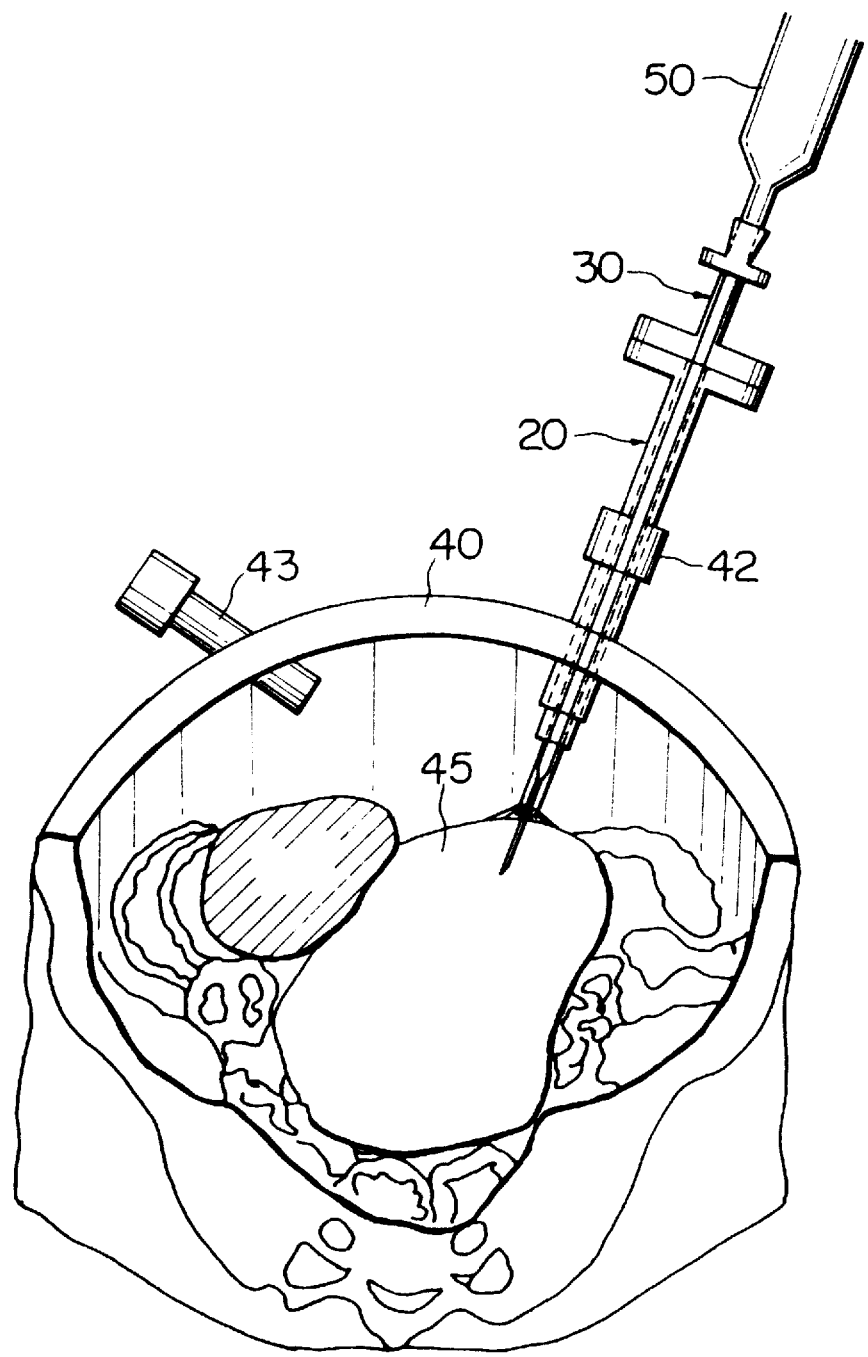
FIG. 26 depicts the transverse sectional view of the FIG. 25.
Figure 27:
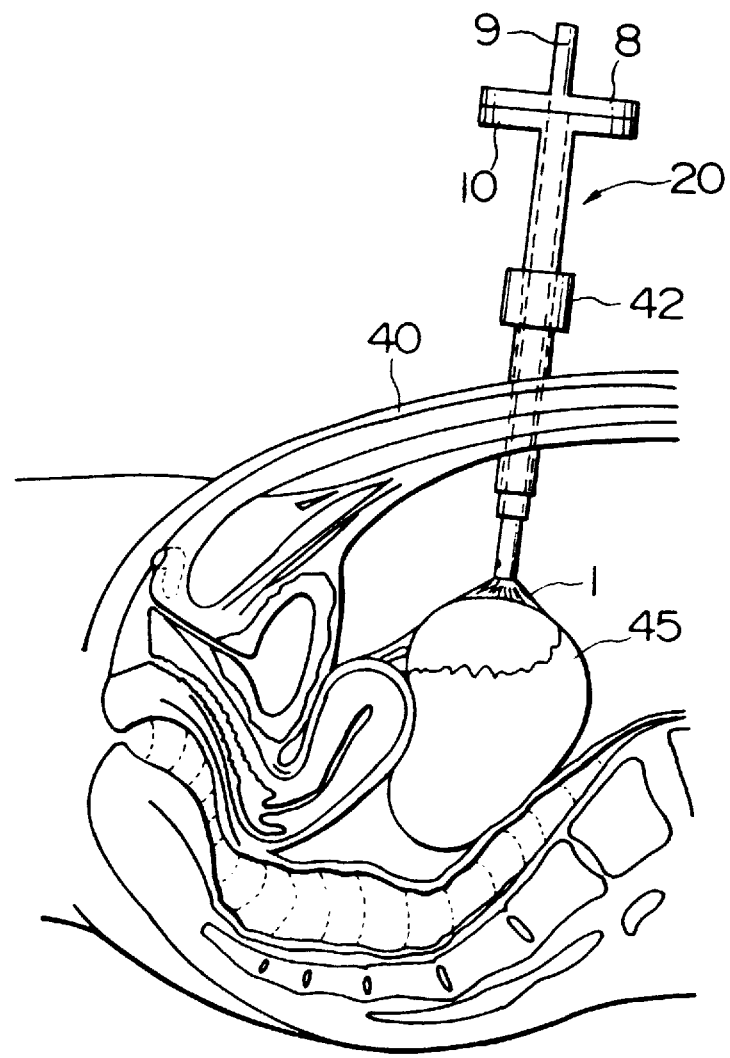
FIG. 27 depicts the longitudinal sectional view in the abdomen after aspiration when the needle body is removed.

Drawing only the bar-like part 32 from the tubular needle part 31 while in such state, inserting aspirator 50 into insertion part 33 of the tubular needle part 31 for carrying out aspiration, as shown in FIGS. 25 and 26, the fluid and the like in the site to be punctured 45 are aspirated into the aspirator 50, whereby sampling is completed.

Figure 28:
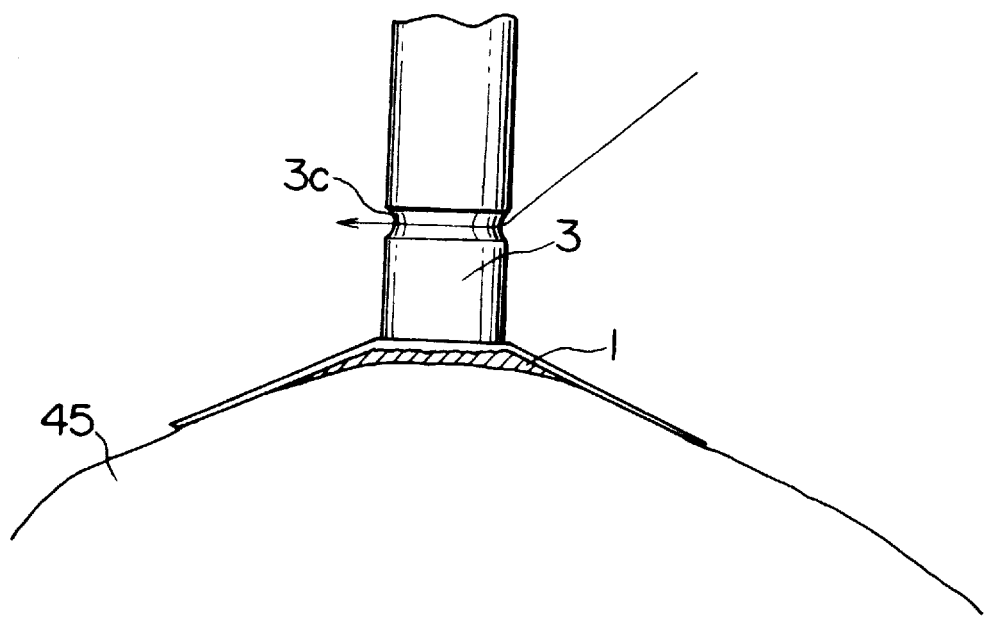
FIG. 28 is a view of a portion of the tubular body prior to cutting.
Figure 29:
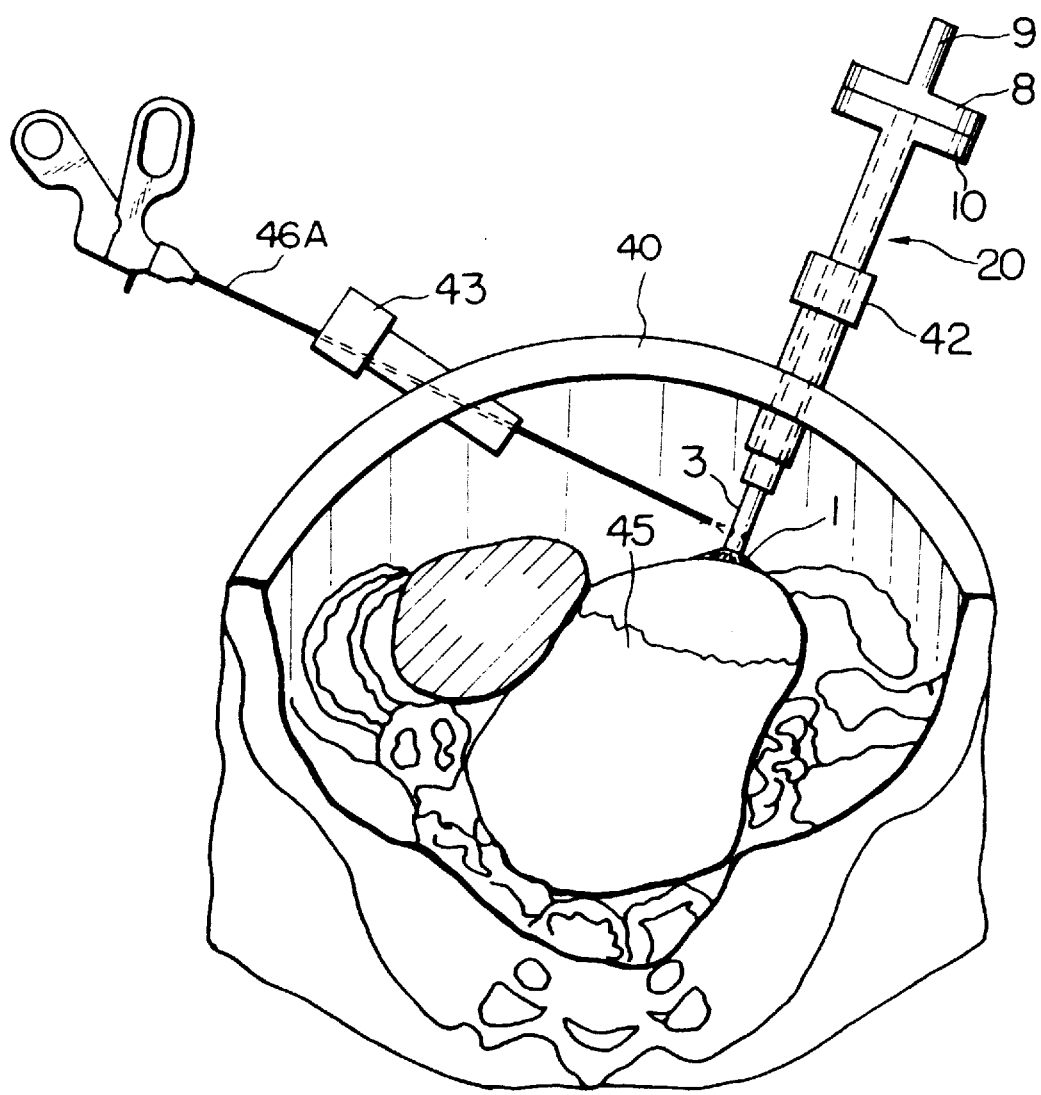
FIG. 29 depicts the transverse sectional view of the abdomen showing the cutting means.

After completion of the aspiration and, drawing out the tubular needle part 31, a cutting means 46A composed of a scissor is inserted into the wall body 40, as shown in FIGS. 28 and 29, to cut recessed groove part 3c of the tubular body 3 while the parasol part 1 is fixed to the site to be punctured 45. Only a part of the tubular body 3 and the parasol part 1 are left fixed to the site to be punctured 45. In such case, the shape of the site to be punctured 45 is in the compact shape compared with the original shape. Furthermore, because the opening left on the sealing part 3A after drawing out the needle body 30 is occluded by means of the shrinking action of the elastic body, the leak of the fluid and the like in the site to be punctured 45 to the outside (namely, endoabdominal region) can be prevented.

Figure 30:
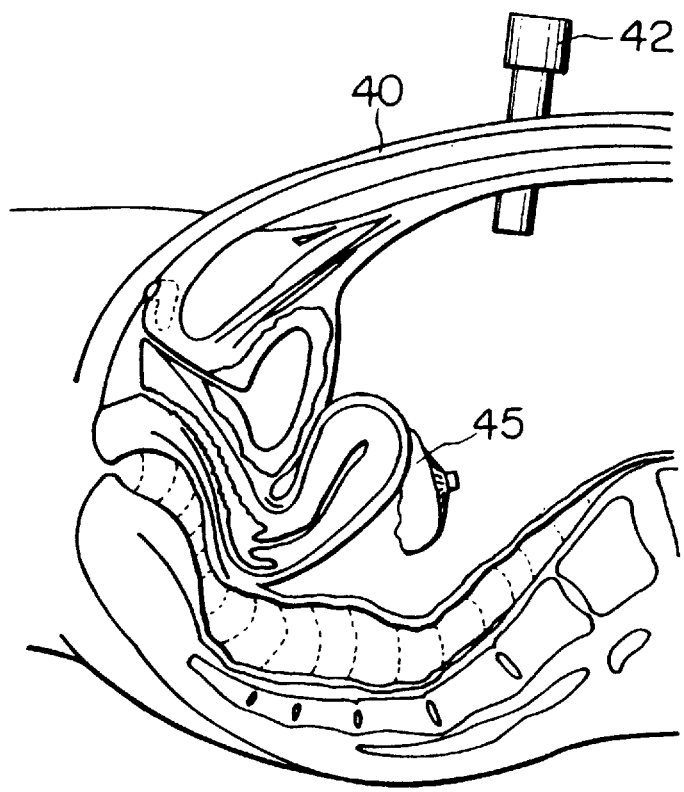
FIG. 30 depicts the longitudinal sectional view of the abdomen after the puncture system is removed.
Figure 31:
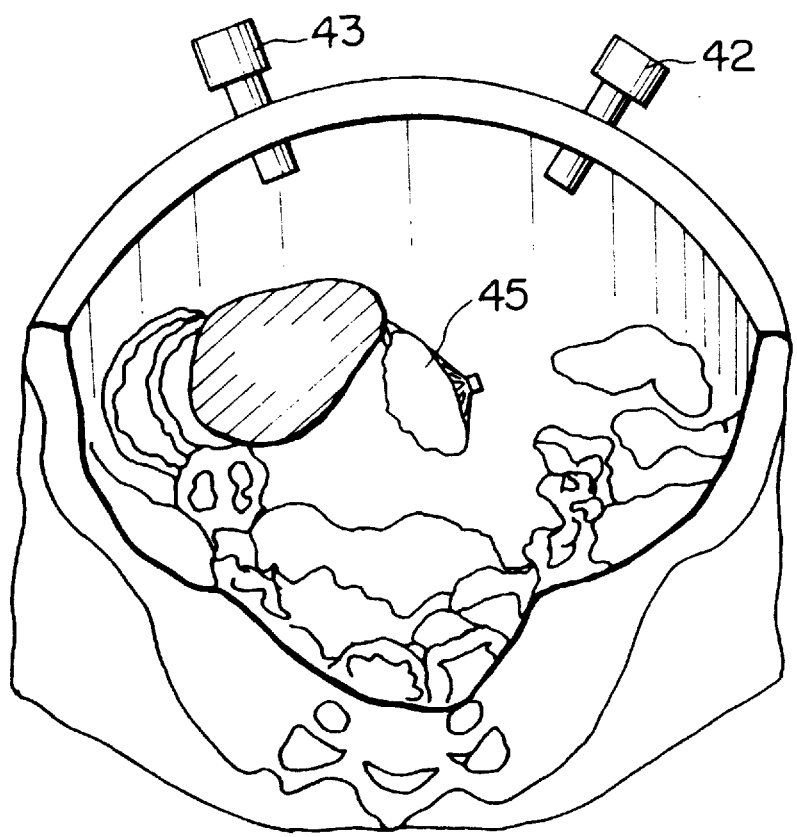
FIG. 31 depicts the transverse sectional view of FIG. 30.

Then, it should be determined whether or not the fluid and the like in the site to be punctured 45 is malignant and which operative technique should be adopted. When it is diagnosed that the sample is benign, the site to be punctured 45 should be resected. Concurrently with the resection of the site 45, the remaining parasol part 1 and the like should be removed from the body as shown in FIGS. 30 and 31. When the fluid and the like are malignant, alternatively, the site to be punctured 45 is resected while being enclosed by a bag (not shown) to prevent the spread of the fluid and the like into the endoabdominal region. Thus, the metastasis of a malignant cancer, if any, to other organs can be prevented. Furthermore, coating the tip of the needle body 30 with silicone coating so as to avoid the adhesion of an adhesive, the needle body 30 is advantageously passed through the sealing part 3A.

Figure 32:
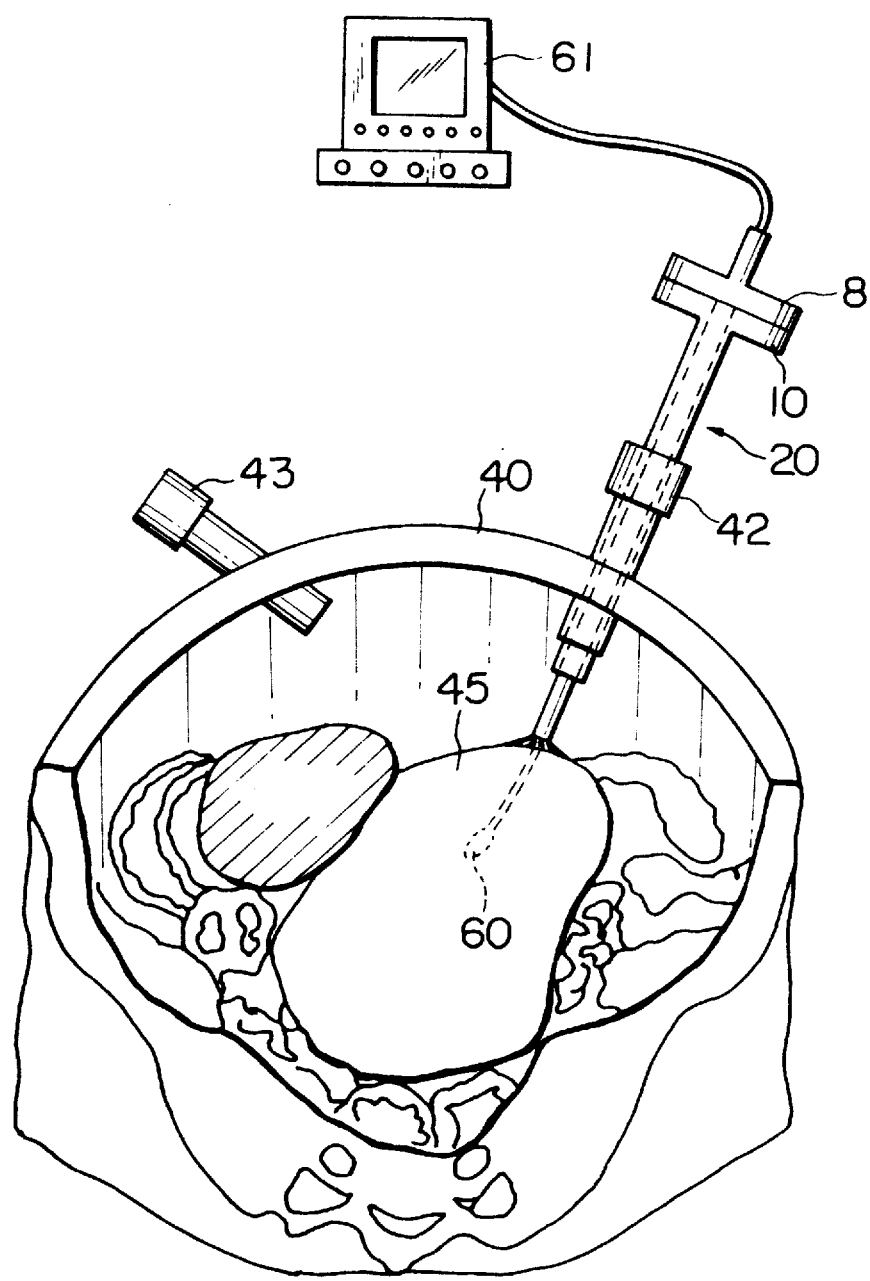
FIG. 32 depicts the transverse sectional view of the abdomen showing an embodiment using a camera.

In another example by inserting camera 60 instead of the aspirator 50 into the site to be punctured 45, as shown in FIG. 32, the inside can be examined by means of monitor TV 61 for establishing the diagnosis.

Figure 33:
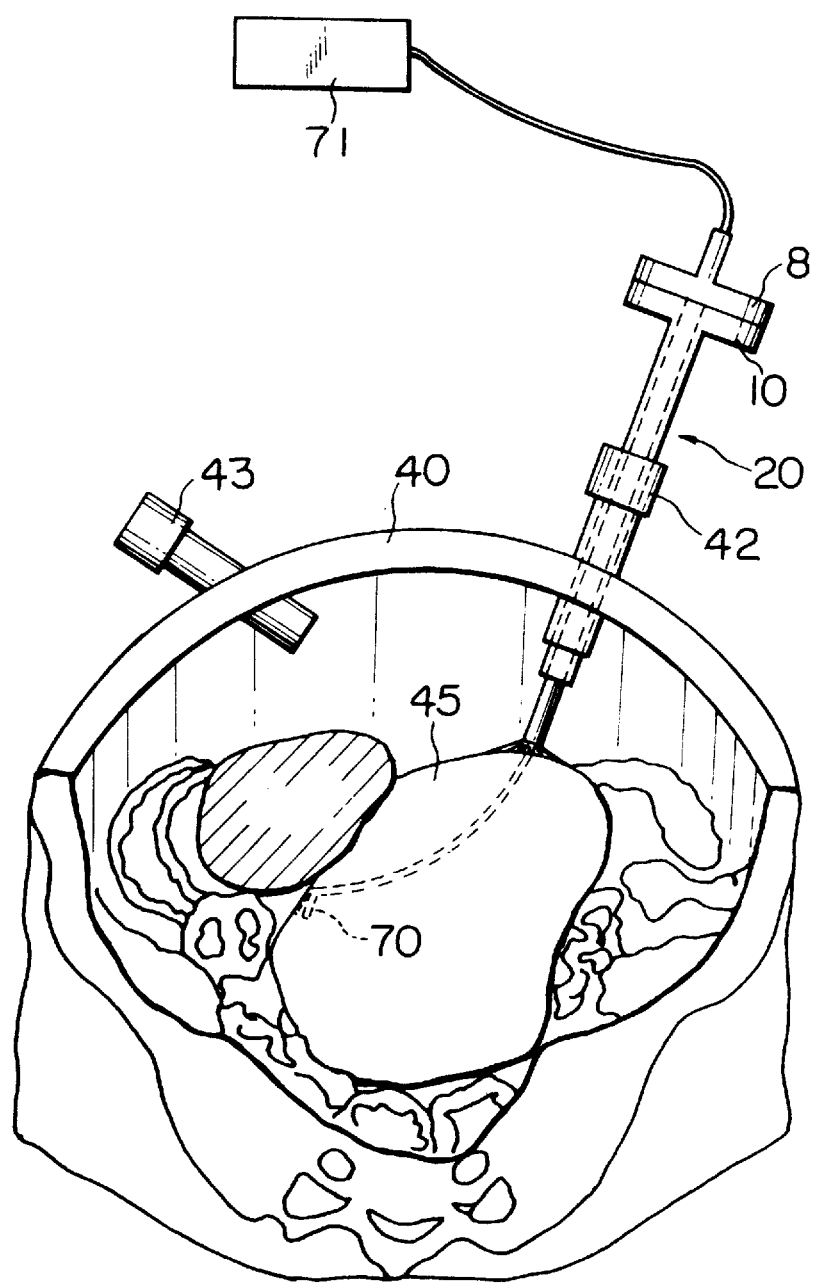
FIG. 33 depicts the transverse sectional view of the abdomen showing an embodiment using a sample collector.

As shown in FIG. 33, furthermore, inserting a well known sample collector 70 instead of the camera 60 and controlling the sample collector 70 by means of a remote controller 71, a biological specimen may be drawn out from the site to be punctured 45.

Figure 5:
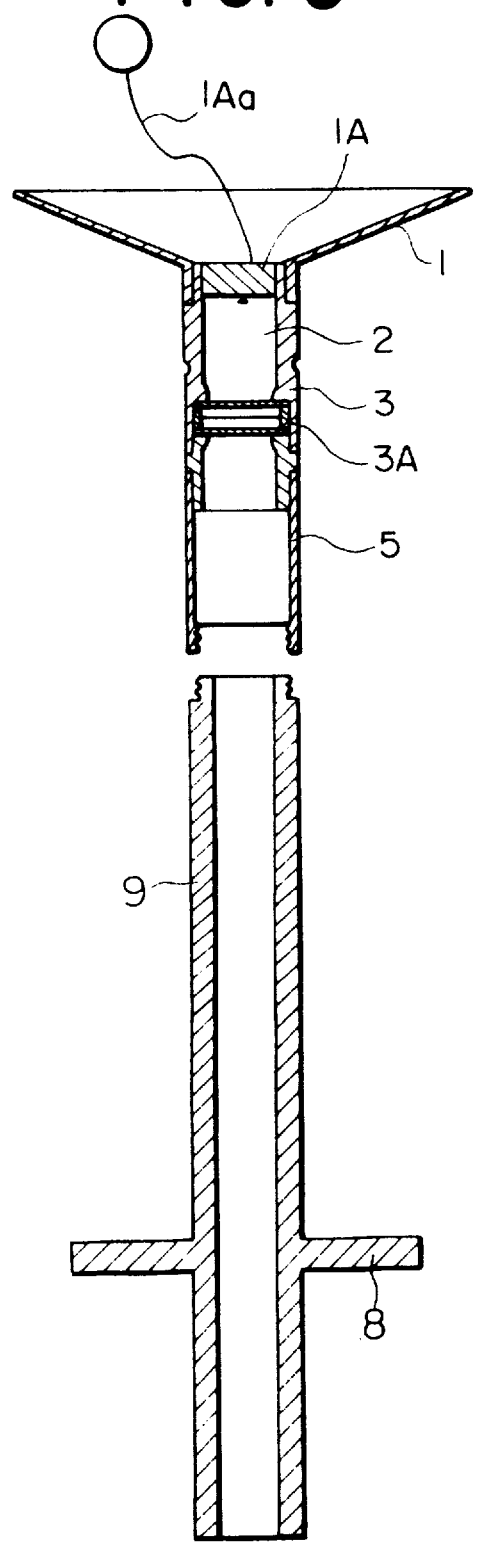
FIG. 5 depicts the structurally decomposed view of the system of FIG. 1, for arranging a first tubular body.

The above example describes the surgery of a human body. It is needless to say that the above example may be applied also to animals, with no specific limitation to humans. The above example describes the surgery by means of laparascope 41. If such laparascope 41 is not used, however, the system does not require the second tubular body 11 but requires the tubular body 3 and the first tubular body 9, as shown in FIG. 5. Incidentally, The present invention is not limited to the foregoing embodiment, but may be applicable to the following embodiments, as well.

Figure 34:
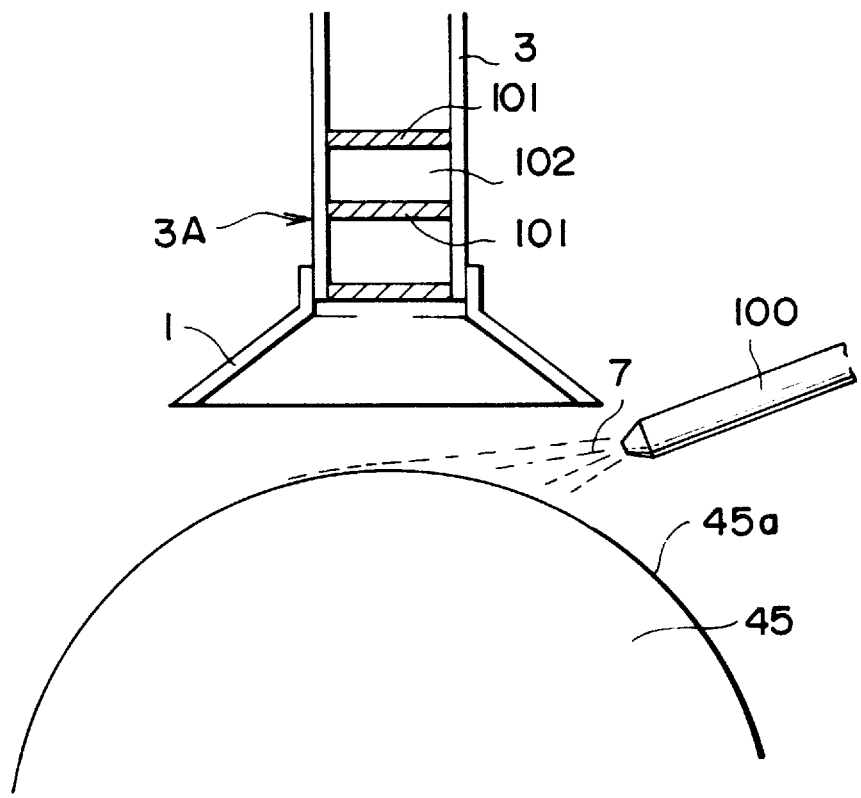
FIG. 34 is a structural view of another embodiment.
Figure 35:
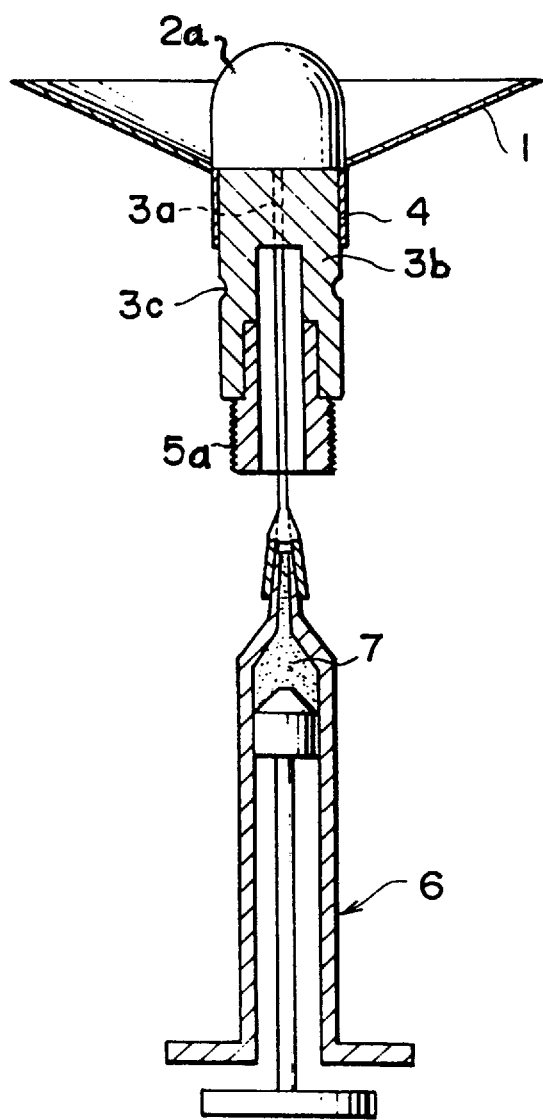
FIG. 35 is a sectional view of another embodiment.
Figure 36:
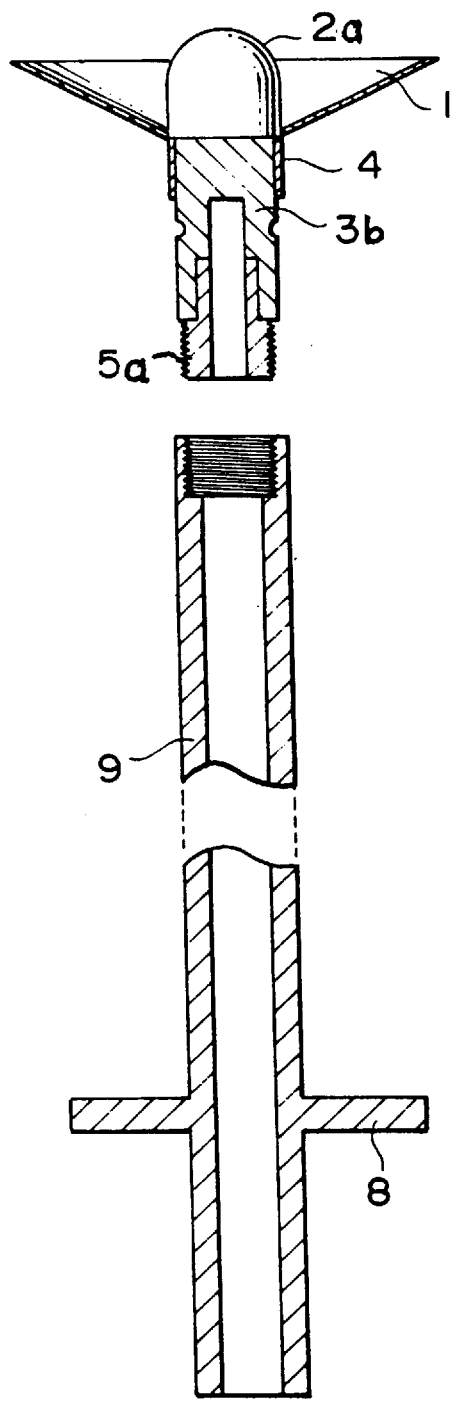
FIG. 36 is a sectional view of a further embodiment.
Figure 37:
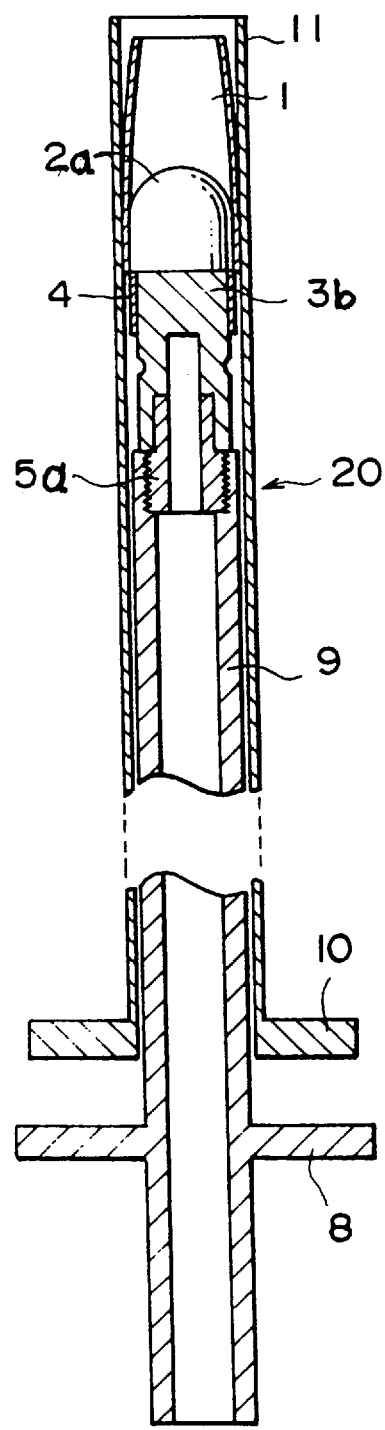
FIG. 37 is a sectional view of a still further embodiment.
Figure 38:
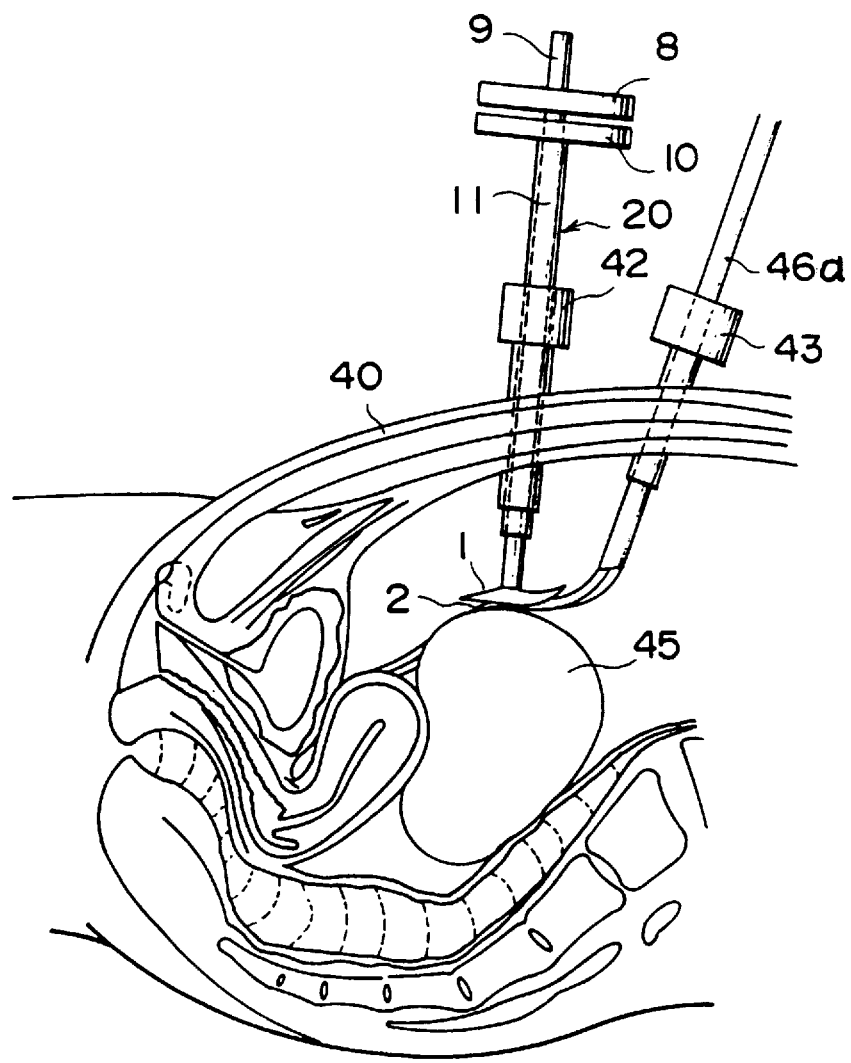
FIG. 38 depicts the sectional view of the abdomen during surgery condition.

Then, Instead of the reservoir 2 employing the plug 1A in the above-mentioned first embodiment, as shown in FIG. 34 illustrating a second embodiment, an adhesive feeding jig 100 containing the adhesive may be inserted into the peritoneal cavity to feed the adhesive 7 onto the puncture site or the parasol part 1 without use of the reservoir 2 and the plug 1A. In the embodiment of Fig. 34, the sealing part 3A of the tubular body 3 includes a pair of sealing plates 101. Ethyl alcohol can be contained within the region 102 between the sealing plates 101. Further, in a third embodiment illustrated in FIG. 35, a tubular body 4 made of corrosion-resisting aluminum or the like is fitted to an outer periphery of the elastic holder body 3b, so that pressure is applied to the elastic holder body 3b from its outer peripheral side by the tubular body 4 to squeeze and shrink a port 3a formed after the puncture by the needle body or the like for restoration to its original state. A tubular threaded body 5a made of corrosion-resisting aluminum or the like is disposed at the lower end of the elastic holder body. Incidentally, the adhesive, such as surgical Allon-alfa, and is injected into the bag part 2a, which may be substituted for the reservoir 2, by an injection appliance 6 immediately prior to usage. Accordingly, the bag part 2a is constructed as shown in FIG. 36 and 37. For practical surgery, as shown in FIG. 38, the bag part 2 is broken within the peritoneal cavity by using cutting means 46a to feed the adhesive 7 for bonding the parasol part 1 to the site to be punctured, so that the procedure similar to that of the first embodiment can be performed.

Because the puncture method and puncture system in accordance with the present invention are composed as described above, the following advantages may be brought about.

Because a parasol part adheres through an adhesive to a site to be punctured and a needle body is then inserted through the sealing part, the opening of the sealing part is shrunk and occluded after drawing out the needle body, to prevent the outward leak of the fluid and the like in the site to be punctured.

The insertion of a camera and a sample collector can be done through the needle body, whereby a wide variety of the applications can be achieved in medical fields.

I claim:

1. A method for puncturing a site on an internal body organ with an instrument having a tubular body with a proximal end and a distal end, a sealing portion proximate the distal end for sealing at least a portion of the tubular body, and a resilient parasol portion extending from the distal end, the method comprising:

inserting the distal end of the tubular body including the parasol portion into a body cavity containing the organ;

advancing the parasol portion within the body cavity to the site;

supplying an adhesive onto one of the site and the parasol portion;

adhering the parasol portion to the site with the adhesive; and puncturing the site by inserting a needle body through the sealing portion of the tubular body and through the site.

2. The method according to claim 1, wherein the parasol portion has a normally opened position and the first tubular body is contained within a second tubular body having a distal portion, the second tubular body compressing the resilient parasol portion into a closed position when the parasol portion is contained within the second tubular body, the method further comprising inserting the distal portion of the second tubular body through a wall of the body cavity, and advancing the distal end of the first tubular body, including the parasol portion, out of the distal portion of the second tubular body, thereby allowing the parasol portion to return to its normally opened position within the body cavity.

3. The method according to claim 2, further comprising aspirating fluid from the organ through the needle body.

4. The method according to claim 2, further comprising inserting a camera through the needle body and observing the inside of the organ.

5. The method according to claim 2, further comprising inserting a sample collector through the needle body and collecting a part of the inside of the site by the sample collector.

6. The method according to claim 2, further comprising cutting the tubular body proximate the distal end and leaving the distal end of the tubular body and the parasol portion on the site.

7. A method according to claim 2, wherein the adhesive is provided in a bag extending from the distal end, the method further comprising supplying the adhesive by cutting the bag to release the adhesive.

8. The method according to claim 2, further comprising inserting an adhesive feeding jig into the body cavity and supplying the adhesive from the adhesive feeding jig.

9. The method according to claim 2, wherein the adhesive is provided in a reservoir within the tubular body, the reservoir being sealed by a plug, the method further comprising supplying the adhesive by removing the plug from the tubular body.

10. The method of claim 2, further comprising drying the site prior to adhering the parasol portion to the site.

11. The method of claim 2, wherein the parasol portion has an inner surface, the method further comprising supplying the adhesive to the inner surface and adhering the inner surface to the site.

12. The method according to claim 1, further comprising aspirating fluid from within the organ through the needle body.

13. The method according to claim 1, further comprising inserting a camera through the needle body and observing the inside of the organ.

14. The method according to claim 1, further comprising inserting a sample collector through the needle body and collecting a part of the inside of the organ by the sample collector.

15. The method according to claim 1, further comprising cutting the tubular body proximate the distal end and leaving the distal end of the tubular body and the parasol portion on the site.

16. The method according to claim 1, wherein the parasol portion has an opened and a closed position and the adhesive is provided in a bag extending from the distal end of the first tubular body, within a region defined by an inner surface of the parasol portion when the parasol portion is in the closed position, the method further comprising opening the parasol portion when the parasol portion is within the body cavity and supplying the adhesive by cutting the bag to release the adhesive.

17. The method according to claim 1, further comprising inserting an adhesive feeding jig into the body cavity and supplying the adhesive from the adhesive feeding jig.

18. The method according to claim 1, wherein the adhesive is provided in a reservoir within the tubular body, the reservoir being sealed by a plug, the method further comprising supplying the adhesive by removing the plug from the tubular body.

19. The method of claim 1, further comprising drying the site prior to adhering the parasol portion to the site.

20. The method of claim 1, wherein the parasol portion has an inner surface, the method further comprising supplying the adhesive to the inner surface and adhering the inner surface to the site.

21. A method for puncturing a site on an internal body organ comprising:
    inseting a distal end of a tubular body into a body cavity containing the organ, the distal end having a resilient parasol portion extending therefrom;
    adhering a surface of the parasol to the site on the internal body organ; and
    inserting a needle body through the tubular body and through the site, thereby puncturing the site.

22. The method of claim 21, wherein the parasol portion has a normally opened and a closed condition, the method further comprising inserting the parasol portion into the body cavity in the closed condition and then opening the parasol portion within the body cavity prior to adhering the parasol portion to the site.

23. The method of claim 22, further comprising applying adhesive to the site prior to adhering the parasol portion to the site.

24. The method of claim 23, further comprising drying the site prior to applying the adhesive.

25. The method of claim 22, further comprising applying adhesive to the surface of the parasol portion prior to adhering the surface of the parasol portion to the site.

26. The method of claim 25, further comprising drying the site prior to adhering the surface of the parasol portion to the site.

27. The method of claim 21, further comprising aspirating fluid from within the organ through the needle body.

28. The method of claim 27, further comprising cutting a portion of the tubular body proximate the parasol portion and leaving the cut portion of the tubular body and the parasol portion on the site, after aspirating the fluid.

29. The method of claim 21, further comprising cutting a portion of the tubular body proximate the parasol portion and leaving the cut portion of the tubular body and the parasol portion on the site, after puncturing the site.

* * * * *

UNITED STATES PATENT AND TRADEMARK OFFICE
CERTIFICATE OF CORRECTION

PATENT NO. : 5,882,331
DATED : March 16, 1999
INVENTOR(S) : Hiroshi Sasaki

It is certified that error appears in the above-identified patent and that said Letters Patent is hereby corrected as shown below:

Column 1, line 46, change "flooded" to --folded--;

Column 2, line 63, delete "puncturing state";

Column 4, line 48, change "to, inserting" to --and, a--;

Same line, change "s" to --is--;

Column 4, line 49, remove "instead";

Column 5, line 53, remove "Then,";

Column 6, line 5, remove ", and";

Signed and Sealed this

Fourteenth Day of November, 2000

Attest:

Q. TODD DICKINSON

*Attesting Officer*  *Director of Patents and Trademarks*